(12) United States Patent
Iwasawa et al.

(10) Patent No.: US 12,708,741 B2
(45) Date of Patent: Aug. 18, 2026

(54) MEDICAL DEVICE AND BENDABLE UNIT

(71) Applicant: CANON KABUSHIKI KAISHA, Tokyo (JP)

(72) Inventors: Ryo Iwasawa, Kanagawa (JP); Atsushi Takasaka, Tokyo (JP); Yusuke Niikawa, Kanagawa (JP); Tomio Noguchi, Shizuoka (JP); Isao Matsuoka, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 501 days.

(21) Appl. No.: 18/358,779

(22) Filed: Jul. 25, 2023

(65) Prior Publication Data

US 2023/0372666 A1 Nov. 23, 2023

Related U.S. Application Data

(63) Continuation of application No. PCT/JP2022/001875, filed on Jan. 20, 2022.

(30) Foreign Application Priority Data

Jan. 27, 2021 (JP) ................................ 2021-011291
Feb. 10, 2021 (JP) ................................ 2021-020059

(51) Int. Cl.
*A61M 5/172* (2006.01)
*A61M 25/00* (2006.01)
(Continued)

(52) U.S. Cl.
CPC ........ *A61M 25/0021* (2013.01); *A61M 39/12* (2013.01)

(58) Field of Classification Search
CPC .......... A61M 25/0147; A61M 25/0105; A61M 25/0133; A61B 34/30; A61B 34/71;
(Continued)

(56) References Cited

U.S. PATENT DOCUMENTS 10,653,489 B2 5/2020 Kopp
2015/0057537 A1 2/2015 Dillon et al.
(Continued)

FOREIGN PATENT DOCUMENTS

CN 105473048 A 4/2016
CN 111358413 A 7/2020
(Continued)

OTHER PUBLICATIONS

EP3508160A1, Inventor-Xu (Year: 2019).*

*Primary Examiner* — Wesley G Harris
*Assistant Examiner* — Charles W Nichols
(74) *Attorney, Agent, or Firm* — Canon U.S.A., Inc. IP Division

(57) ABSTRACT

A medical device 1 includes a main body driving unit (300) including a plurality of driving sources (M11 to M33), a base unit (200) including a coupling device (21) connected to the main body driving unit, a bendable unit (100) configured to be detachably attached to the base unit, and an operation unit (400) configured to be movable between a fixed position and a detachment position. The base unit includes a plurality of coupling units (21*c*11 to 21*c*33). The bendable unit includes a plurality of linear members (W11 to W33). A state where each of the plurality of linear members is fixed by each of the plurality of coupling units and a state where each of the plurality of linear members is unfixed from each of the plurality of coupling units are switched in an interlocked manner with movement of the operation unit.

14 Claims, 17 Drawing Sheets

(51) Int. Cl.
*A61M 39/12* (2006.01)
*G16H 20/17* (2018.01)

(58) Field of Classification Search
CPC .... A61B 2017/00323; A61B 2034/301; A61B 1/0016; A61B 1/0052; A61B 1/0057
See application file for complete search history.

(56) References Cited

U.S. PATENT DOCUMENTS

| | | | | |
|---|---|---|---|---|
| 2016/0074625 | A1* | 3/2016 | Furnish ............. | A61M 25/0133 604/95.04 |
| 2020/0337792 | A1 | 10/2020 | Zemlok | |
| 2020/0375677 | A1* | 12/2020 | Genova .................. | A61B 17/29 |

FOREIGN PATENT DOCUMENTS

| | | | | |
|---|---|---|---|---|
| EP | 3508160 | A1 * | 7/2019 | ....... A61B 17/00234 |
| EP | 3539501 | A1 | 9/2019 | |
| JP | 2011019792 | A | 2/2011 | |
| JP | 2013248117 | A | 12/2013 | |
| JP | 2015136375 | A | 7/2015 | |
| JP | 2016532504 | A | 10/2016 | |
| JP | 2020054446 | A | 4/2020 | |
| WO | 2015/026557 | A1 | 2/2015 | |

* cited by examiner

MEDICAL DEVICE AND BENDABLE UNIT

CROSS-REFERENCE TO RELATED APPLICATIONS

This application is a Continuation of International Patent Application No. PCT/JP2022/001875, filed Jan. 20, 2022, which claims the benefit of Japanese Patent Applications No. 2021-011291, filed Jan. 27, 2021, and No. 2021-020059, filed Feb. 10, 2021, all of which are hereby incorporated by reference herein in their entirety.

BACKGROUND OF THE INVENTION

Field of the Invention

The present invention relates to a medical device and a bendable unit used for the medical device.

Background Art

Japanese Patent Application Laid-Open No. 2013-248117 discusses a medical tool that includes a unit to be operated including a deformable portion and an operation unit for deforming the deformable portion, wherein the unit to be operated and the operation unit are detachably attachable.

CITATION LIST

Patent Literature

PTL 1: Japanese Patent Application Laid-Open No. 2013-248117

According to Japanese Patent Application Laid-Open No. 2013-248117, the operation unit is detached from the unit to be operated in a state where force for fixing the operation unit to the unit to be operated is acting on the operation unit.

SUMMARY OF THE INVENTION

An object of the present invention is to provide a bendable unit that includes a plurality of linear members and can be easily attached to and detached from a base unit by a user, and a medical device including the same.

According to an aspect of the present invention of the present application, a medical device includes a main body driving unit including a plurality of driving sources, a base unit including a coupling device connected to the main body driving unit, the coupling device including a plurality of coupling units, each of the plurality of coupling units being connected to each of the plurality of driving sources, a bendable unit configured to be detachably attached to the base unit, the bendable unit including a bending unit and a bending driving unit configured to receive driving force of the main body driving unit via the coupling device and bend the bending unit, the bending driving unit including a plurality of linear members connected to the bending unit, and an operation unit configured to be movable between a fixed position and a detachment position in a state where the bendable unit is attached to the base unit, wherein a state where each of the plurality of linear members is fixed by each of the plurality of coupling units and a state where each of the plurality of linear members is unfixed from each of the plurality of coupling units are switched in an interlocked manner with movement of the operation unit, wherein each of the plurality of linear members is fixed to each of the plurality of coupling units so that detachment of the bendable unit from the base unit is restricted and the driving force is transmitted to the bending driving unit in a state where the bendable unit is attached to the base unit and the operation unit is located at the fixed position, and wherein the detachment of the bendable unit from the base unit is allowed and each of the plurality of linear members is unfixed from each of the plurality of coupling units in a state where the bendable unit is attached to the base unit and the operation unit is located at the detachment position.

According to an aspect of the present invention of the present application, a bendable unit configured to be detachably attached to a base unit, the base unit including a main body driving unit including a plurality of driving sources, and a coupling device connected to the main body driving unit, the coupling device including a plurality of coupling units, each of the plurality of coupling units being connected to each of the plurality of driving sources, includes a bending unit, a bending driving unit configured to receive driving force of the main body driving unit via the coupling device and bend the bending unit, the bending driving unit including a plurality of linear members connected to the bending unit, and an operation unit configured to be movable between a fixed position and a detachment position in a state where the bendable unit is attached to the base unit, wherein a state where each of the plurality of linear members is fixed by each of the plurality of coupling units and a state where each of the plurality of linear members is unfixed from each of the plurality of coupling units are switched in an interlocked manner with movement of the operation unit, wherein each of the plurality of linear members is fixed to each of the plurality of coupling units so that detachment of the bendable unit from the base unit is restricted and the driving force is transmitted to the bending driving unit in a state where the bendable unit is attached to the base unit and the operation unit is located at the fixed position, and wherein the detachment of the bendable unit from the base unit is allowed and each of the plurality of linear members is unfixed from each of the plurality of coupling units in a state where the bendable unit is attached to the base unit and the operation unit is located at the detachment position.

As described above, according to the present invention, a bendable unit that includes a plurality of linear members and can be easily attached to and detached from a base unit by a user, and a medical device including the same can be provided.

Further features of the present invention will become apparent from the following description of exemplary embodiments with reference to the attached drawings.

DESCRIPTION OF THE EMBODIMENTS

A configuration of the present invention will be described below with reference to the drawings. It should be noted that dimensions, materials, shapes and arrangement of components described in the present exemplary embodiment are subject to appropriate changes depending on the configuration of apparatuses to which the present invention is applied and various conditions.

First Exemplary Embodiment

<Medical System and Medical Device>

Figure 1:
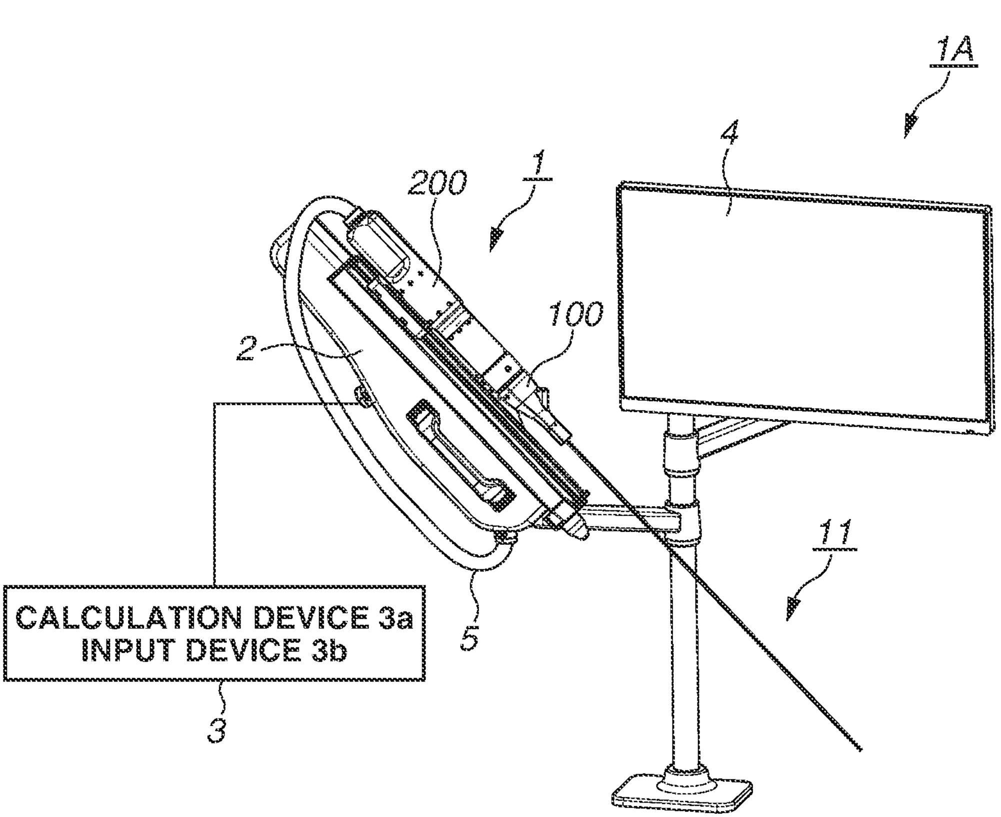
FIG. 1 is an overall view of a medical system.
Figure 2:
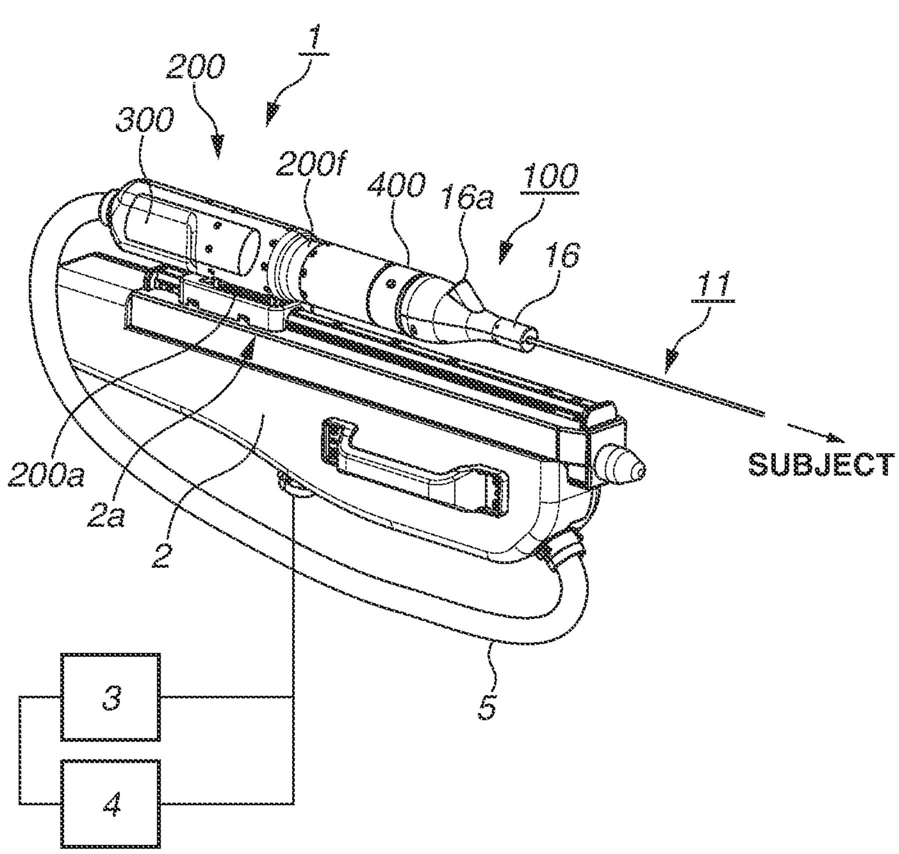
FIG. 2 is a perspective view illustrating a medical device and a support.

A medical system 1A and a medical device 1 will be described with reference to FIGS. 1 and 2. FIG. 1 is an overall view of the medical system 1A. FIG. 2 is a perspective view illustrating the medical device 1 and a support 2.

The medical system 1A includes the medical device 1, the support 2 to which the medical device 1 is attached, and a control device 3 that controls the medical device 1. In the present exemplary embodiment, the medical system 1A include a monitor 4 serving as a display device.

The medical device 1 includes a catheter unit (bendable unit) 100 including a catheter 11 serving as a bendable body, and a base unit (driving unit, unit to be attached) 200. The catheter unit 100 is configured to be detachably attachable to the base unit 200.

In the present exemplary embodiment, a user of the medical system 1A and the medical device 1 can perform operations such as observation of the interior of a subject, sampling of various specimens from the interior of the subject, and treatment to the interior of the subject by inserting the catheter 11 into the interior of the subject. As an exemplary embodiment, the user can insert the catheter 11 into the interior of a patient who is the subject. Specifically, the user can perform operations such as observation, sampling, excision, and the like of lung tissue by inserting the catheter 11 into a bronchus via the mouth cavity or nasal cavity of the patient.

The catheter 11 can be used as a guide (sheath) for guiding medical tools for performing the foregoing operations. Examples of the medical tools include an endoscope, forceps, and an abrasion device. The catheter 11 itself may have the functions of the foregoing medical devices.

In the present exemplary embodiment, the control unit 3 includes a calculation device 3*a* and an input device 3*b*. The input device 3*b* receives instructions and inputs for operating the catheter 11. The calculation device 3*a* includes a storage storing programs for controlling the catheter and various types of data, a random access memory, and a central processing unit for executing the programs. The control unit 3 may include an output unit that outputs a signal for displaying an image on the monitor 4.

As illustrated in FIG. 2, in the present exemplary embodiment, the medical device 1 is electrically connected to the control unit 3 via a cable 5, which couples the base unit 200 of the medical device 1 to the support 2, and the support 2. The medical device 1 and the control unit 3 may be directly connected by a cable. The medical device 1 and the control unit 3 may be wirelessly connected.

The medical device 1 is detachably attached to the support 2 via the base unit 200. More specifically, an attachment unit (connection unit) 200*a* of the base unit 200 is detachably attached to a moving stage (receptor unit) 2*a* of the support 2. Even in a state where the attachment unit 200*a* of the medical device 1 is detached from the moving stage 2*a*, the connection between the medical device 1 and the control unit 3 is maintained so that the medical device 1 can be controlled by the control unit 3. In the present exemplary embodiment, the medical device 1 and the support 2 are connected by the cable 5 even in the state where the attachment unit 200*a* of the medical device 1 is detached from the moving stage 2*a*.

In the state where the medical device 1 is detached from the support 2 (where the medical device 1 is detached from the moving stage 2*a*), the user can manually move the medical device 1 and insert the catheter 11 into the interior of the subject.

The user can use the medical device 1 in a state where the catheter 11 is inserted into the subject and the medical device 1 is attached to the support 2. Specifically, in the state where the medical device 1 is attached to the moving stage 2*a*, the moving state 2*a* moves to move the medical device 1. An operation of moving the catheter 11 in a direction of insertion into the subject and an operation of moving the catheter 11 in a direction of withdrawal from the subject are then performed. The movement of the moving stage 2*a* is controlled by the control unit 3.

The attachment unit 200*a* of the base unit 200 includes a not-illustrated unlock switch and detachment switch. In the state where the attachment unit 200*a* is attached to the moving stage 2*a*, the user can hold down the unlock switch and manually move the medical device 1 along the direction guided by the moving stage 2*a*. In other words, the moving stage 2*a* includes a guide configuration for guiding the movement of the medical device 1. If the user stops holding down the unlock switch, the medical device 1 is fixed to the moving stage 2*a*. If the detachment switch is pressed in the state where the attachment unit 200*a* is attached to the moving stage 2*a*, the user can detach the medical device 1 from the moving stage 2*a*.

A single switch may have the functions of the unlock switch and the detachment switch. If the unlock switch includes a mechanism by which the unlock switch switches the state of being held down and the state of not being held down, the user does not need to continue pressing the unlock switch during the manual slide movement of the medical device 1.

In a state where the attachment unit 200*a* is attached to the moving stage 2*a* and neither of the unlock and detachment switches is pressed, the medical device 1 is fixed to the moving stage 2*a* and moved by the moving stage 2*a* that is driven by a not-illustrated motor.

The medical device 1 includes a wire driving unit (linear member driving unit, line driving unit, or main body driving unit) 300 for driving the catheter 11. In the present exemplary embodiment, the medical device 1 is a robot catheter device that drives the catheter 11 using the wire driving unit 300 controlled by the control unit 3.

The control device 3 can control the wire driving unit 300 to perform an operation of bending the catheter 11. In the present exemplary embodiment, the wire driving unit 300 is built in the base unit 200. More specifically, the base unit 200 includes a base housing 200*f* accommodating the wire driving unit 300. In other words, the base unit 200 includes the wire driving unit 300. The wire driving unit 300 and the base unit 200 may be referred to collectively as a catheter driving device (base device or main body).

In the extending direction of the catheter 11, an end where the tip of the catheter 11 to be inserted into the subject is located will be referred to as a distal end. In the extending direction of the catheter 11, the end opposite the distal end will be referred to as a proximal end.

The catheter unit 100 includes a proximal end cover 16 that covers the proximal end side of the catheter 11. The proximal end cover 16 has a tool hole 16*a*. A medical tool can be inserted into the catheter 11 via the tool hole 16*a*.

As described above, in the present exemplary embodiment, the catheter 11 has a function as a guide device for guiding the medical tool to a desired position inside the subject.

For example, the catheter 11 is inserted up to a target position inside the subject with an endoscope inserted in the catheter 11. Here, at least one of the following is used: the user's manual operation, the movement of the moving stage 2*a*, and the driving of the catheter 11 by the wire driving unit 300. After the catheter 11 reaches the target position, the endoscope is pulled out of the catheter 11 via the tool hole 16*a*. A medical tool is then inserted from the tool hole 16*a*, and operations such as the sampling of various specimens from the interior of the subject and treatment to the interior of the subject are performed.

As will be described below, the catheter unit 100 is detachably attached to the catheter driving device (base device or main body), or more specifically, the base unit 200. After the medical device 1 is used, the user can detach the catheter unit 100 from the base unit 200, attach a new catheter unit 100 to the base unit 200, and use the medical device 1 again.

As illustrated in FIG. 2, the medical device 1 includes an operation unit 400. In the present exemplary embodiment, the operation unit 400 is provided to the catheter unit 100. The operation unit 400 is operated by the user in fixing the catheter unit 100 to the base unit 200 or detaching the catheter unit 100 from the base unit 200.

With the endoscope inserted into the catheter 11 and the monitor 4 connected, an image captured by the endoscope can be displayed on the monitor 4. With the monitor 4 and the control unit 3 connected, the state of the medical device 1 and information about the control of the medical device 1 can be displayed on the monitor 4. For example, the position of the catheter 11 inside the subject and navigation-related information about the catheter 11 inside the subject can be displayed on the monitor 4. The monitor 4, the control unit 3, and the endoscope may be connected in a wired manner or wirelessly. The monitor 4 and the control unit 3 may be connected via the support 2.

<Catheter>

Figure 3A:
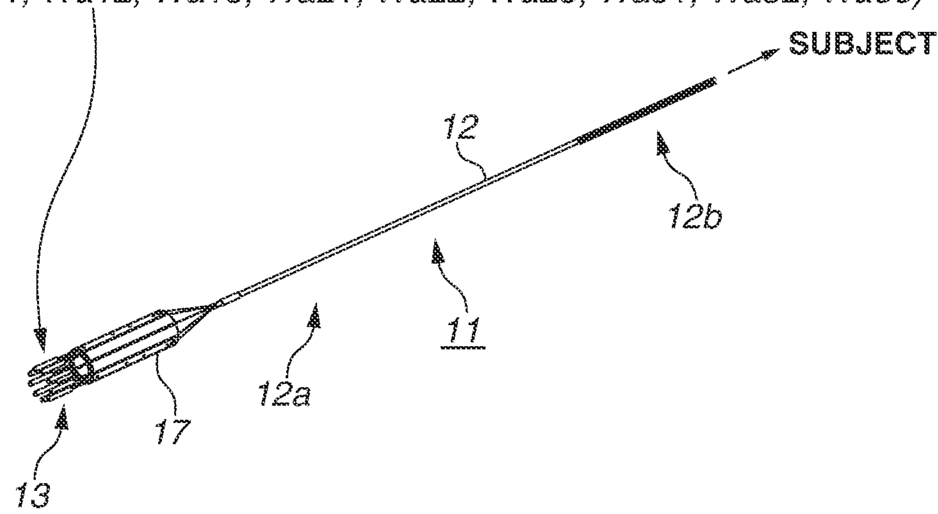
FIG. 3A is an explanatory diagram of a catheter.
Figure 3B:
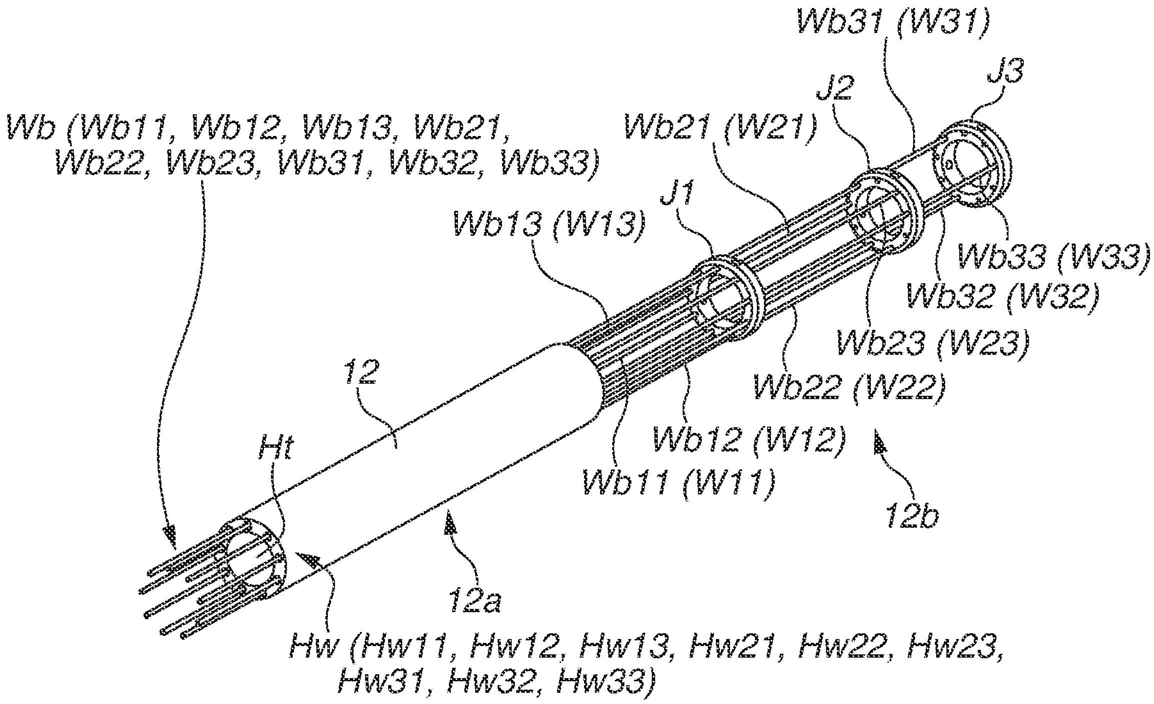
FIG. 3B is an explanatory diagram of the catheter.

The catheter 11 serving as the bendable body will be described with reference to FIGS. 3A and 3B. FIGS. 3A and 3B are explanatory diagrams of the catheter 11. FIG. 3A is a diagram for describing the entire catheter 11. FIG. 3B is an enlarged view of the catheter 11.

The catheter 11 includes a bending unit (bendable body or catheter main body) 12 and a bending driving unit (catheter driving unit) 13 configured to bend the bending unit 12. The bending driving unit 13 is configured to receive driving force from the wire driving unit 300 via a coupling device 21 to be described below and bend the bending unit 12.

The catheter 11 extends in the direction of insertion of the catheter 11 into a subject. The extending direction (longitudinal direction) of the catheter 11 is the same as the extending direction (longitudinal direction) of the bending unit 12 and the extending direction (longitudinal direction) of first to ninth driving wires (W11 to W33) to be described below.

The bending driving unit 13 includes a plurality of driving wires (driving lines, linear members, or linear actuators) connected to the bending unit 12. Specifically, the bending driving unit 13 includes a first driving wire W11, a second driving wire W12, a third driving wire W13, a fourth driving wire W21, a fifth driving wire W22, a sixth driving wire W23, a seventh driving wire W31, an eighth driving wire W32, and a ninth driving wire W33.

The first to ninth driving wires (W11 to W33) each include a portion to be held (shaft to be held, or rod) Wa. Specifically, the first driving wire W11 includes a first portion to be held Wa11. The second driving wire W12 includes a second portion to be held Wa12. The third driving wire W13 includes a third portion to be held Wa13. The fourth driving wire W21 includes a fourth portion to be held Wa21. The fifth driving wire W22 includes a fifth portion to be held Wa22. The sixth driving wire W23 includes a sixth portion to be held Wa23. The seventh driving wire W31 includes a seventh portion to be held Wa31. The eighth driving wire W32 includes an eighth portion to be held Wa32. The ninth driving wire W33 includes a ninth portion to be held Wa33.

In the present exemplary embodiment, the first to ninth portions to be held (Wa11 to Wa33) have the same shape.

The first to ninth driving wires (W11 to W33) each include a flexible wire body (line body or linear body) Wb. Specifically, the first driving wire W11 includes a first wire body Wb11. The second driving wire W12 includes a second wire body Wb12. The third driving wire W13 includes a third wire body Wb13. The fourth driving wire W21 includes a fourth wire body Wb21. The fifth driving wire W22 includes a fifth wire body Wb22. The sixth driving wire W23 includes a sixth wire body Wb23. The seventh driving wire W31 includes a seventh wire body Wb31. The eighth driving wire W32 includes an eighth wire body Wb32. The ninth driving wire W33 includes a ninth wire body Wb33.

In the present exemplary embodiment, the first to third wire bodies (Wb11 to Wb13) have the same shape. The fourth to sixth wire bodies (Wb21 to Wb23) have the same shape. The seventh to ninth wire bodies (Wb31 to Wb33) have the same shape. In the present exemplary embodiment, the first to ninth wire bodies (Wb11 to Wb33) have the same shape except for the lengths.

The first to ninth portions to be held (Wa11 to Wa33) are fixed to the first to ninth wire bodies (Wb11 to Wb33) at the proximal ends of the first to ninth wire bodies (Wb11 to Wb33).

The first to ninth driving wires (W11 to W33) are inserted into and fixed to the bending unit 12 via a wire guide 17.

In the present exemplary embodiment, each of the first to ninth driving wires (W11 to W33) is made of a metal material. However, each of the first to ninth driving wires (W11 to W33) may be made of a resin material. Each of the first to ninth driving wires (W11 to W33) may be made of a material including metal and resin.

Any one of the first to ninth driving wires (W11 to W33) can be referred to as a driving wire W. In the present exemplary embodiment, the first to ninth driving wires (W11 to W33) have the same shape except for the lengths of each of the first to ninth wire bodies (Wb11 to Wb33).

In the present exemplary embodiment, the bending unit 12 is a flexible tube-like member having a passage Ht for inserting a medical tool.

A plurality of wire holes through which each of the first to ninth driving wires (W11 to W33) passes is formed along a wall surface of the bending unit 12. Specifically, a first wire hole Hw11, a second wire hole Hw12, a third wire hole Hw13, a fourth wire hole Hw21, a fifth wire hole Hw22, a sixth wire hole Hw23, a seventh wire hole Hw31, an eighth wire hole Hw32, and a ninth wire hole Hw33 are formed along the wall surface of the bending unit 12. The first to ninth wire holes Hw (Hw11 to Hw33) correspond to the first to ninth driving wires (W11 to W33), respectively. The numerals following the symbols Hw indicate the numbers of the corresponding driving wires. For example, the first driving wire W11 is inserted into the first wire hole Hw11.

Any one of the first to ninth wire holes (Hw11 to Hw33) can be referred to as a wire hole Hw. In the present exemplary embodiment, the first to ninth wire holes (Hw11 to Hw33) have the same shape.

The bending unit 12 includes an intermediate region 12*a* and a bending region 12*b*. The bending region 12*b* is located at the distal end of the bending unit 12. A first guide ring J1, a second guide ring J2, and a third guide ring J3 are disposed in the bending region 12*b*. The bending region 12*b* refers to a region where the magnitude and direction of bending of the bending unit 12 can be controlled by moving the first guide ring J1, the second guide ring J2, and the third guide ring J3 using the bending driving unit 13. In FIG. 3B, a part of the bending unit 12 covering the first to third guide rings (J1 to J3) is omitted.

In the present exemplary embodiment, the bending unit 12 includes a plurality of auxiliary rings (not illustrated). In the bending region 12*b*, the first guide ring J1, the second guide ring J2, and the third guide ring J3 are fixed to the wall surface of the bending unit 12. In the present exemplary embodiment, the plurality of auxiliary rings is located between the first guide ring J1 and the second guide ring J2 and between the second guide ring J2 and the third guide ring J3.

The medical tool is guided to the tip of the catheter 11 by the passage Ht, the first to third guide rings (J1 to J3), and the plurality of auxiliary rings.

Each of the first to ninth driving wires (W11 to W33) passes through the intermediate region 12*a* to be fixed to each of the first to third guide rings (J1 to J3).

Specifically, the first driving wire W11, the second driving wire W12, and the third driving wire W13 are fixed to the first guide ring J1. The fourth driving wire W21, the fifth driving wire W22, and the sixth driving wire W23 passes through the first guide ring J1 and a plurality of auxiliary rings and are fixed to the second guide ring J2. The seventh driving wire W31, the eighth driving wire W32, and the ninth driving wire W33 passes through the first guide ring J1, the second guide ring J2, and the plurality of auxiliary rings and are fixed to the third guide ring J3.

The medical device 1 can bend the bending unit 12 in directions intersecting the extending direction of the catheter 11 by driving the bending driving unit 13 with the wire driving unit 300. Specifically, the bending region 12*b* of the bending unit 12 can be bent in directions intersecting the extending direction via the first to third guide rings (J1 to J3) by moving each of the first to ninth driving wires (W11 to W33) in the extending direction of the bending unit 12.

The user can insert the catheter 11 up to an intended part inside the subject by using at least one of the following manual movement of the medical device 1, movement of the medical device 1 by the moving stage 2*a*, and bending of the bending unit 12.

In the present exemplary embodiment, the bending unit 12 is bent by moving the first to third guide rings (J1 to J3) using the first to ninth driving wires (W11 to W33). However, the present invention is not limited to such a configuration. Any one or two of the first to third guide rings (J1 to J3) and driving wires fixed thereto may be omitted.

For example, the catheter 11 may be configured to include the seventh to ninth driving wires (W31 to W33) and the third guide ring J3, with the first to sixth driving wires (W11 to W23) and the first and second guide rings (J1 and J2) omitted. Alternatively, the catheter 11 may be configured to include the fourth to ninth driving wires (W21 to W33) and the second and third guide rings (J2 and J3), with the first to third driving wires (W11 to W13) and the first guide ring J1 omitted.

The catheter 11 may be configured so that a guide ring is driven by two driving wires. Even in such a case, the number of guide rings may be one or more than one.

<Catheter Unit>

The catheter unit 100 will be described with reference to FIGS. 4A and 4B.

Figure 4A:
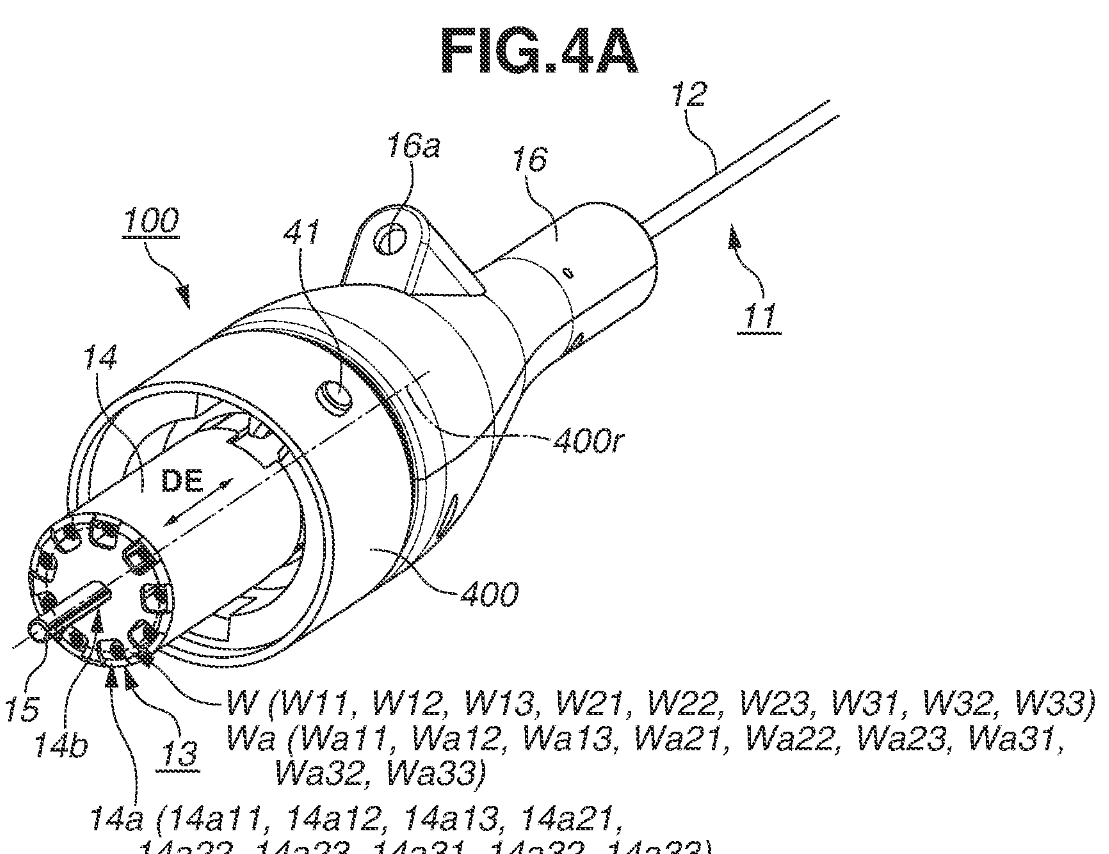
FIG. 4A is an explanatory diagram of a catheter unit.
Figure 4B:
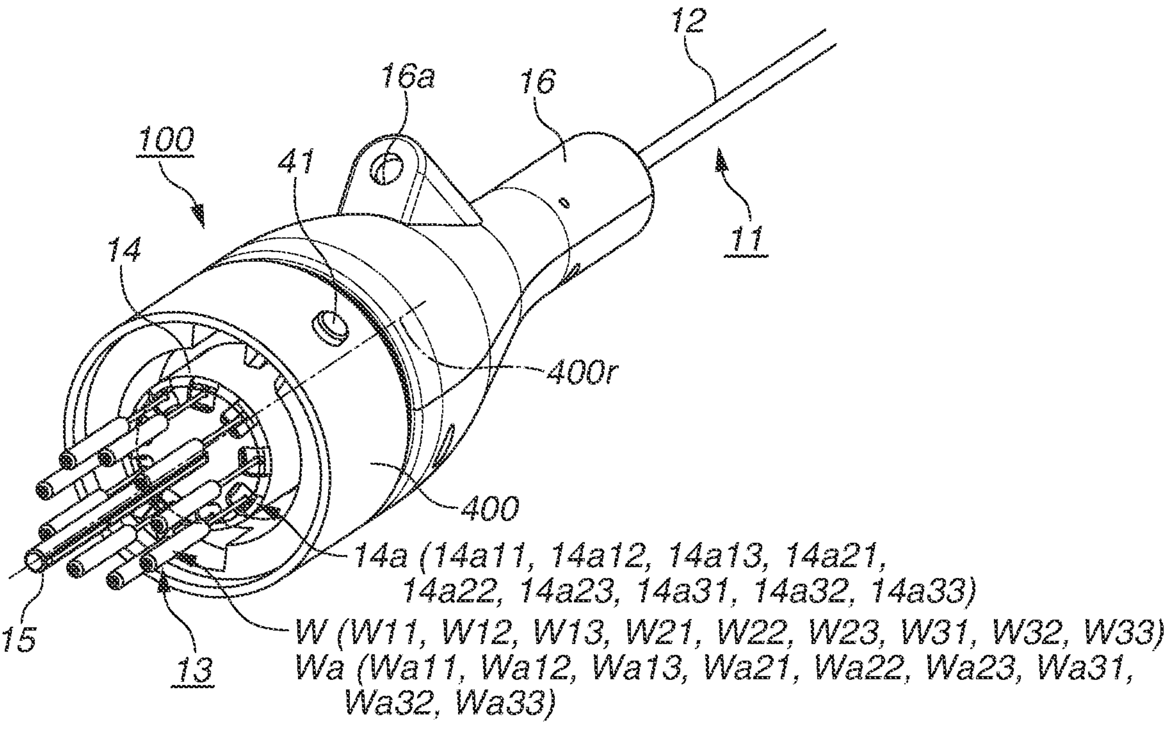
FIG. 4B is an explanatory diagram of the catheter unit.

FIGS. 4A and 4B are explanatory diagrams of the catheter unit 100. FIG. 4A is an explanatory diagram of the catheter unit 100 in a state where a wire cover 14 to be described below is at a cover position. FIG. 4B is an explanatory diagram of the catheter unit 100 in a state where the wire cover 14 to be described below is at an exposure position.

The catheter unit 100 includes the catheter 11 including the bending unit 12 and the bending driving unit 13, and the proximal end cover 16 supporting the proximal end of the catheter 11. The catheter unit 100 includes the cover (wire cover) 14 for covering and protecting the first to ninth driving wires (W11 to W33) serving as the plurality of driving wires.

The catheter unit 100 can be attached to and detached from the base unit 200 along an attachment and detachment direction DE. The attaching direction of the catheter unit 100 to the base unit 200 and the detaching direction of the catheter unit 100 from the base unit 200 are parallel to the attachment and detachment direction DE.

The proximal end cover (frame, bending unit housing, or catheter housing) 16 is a cover covering a part of the catheter 11. The proximal end cover 16 has the tool hole 16*a* for inserting a medical tool into the passage Ht of the bending unit 12.

The wire cover 14 has a plurality of exposure holes (wire cover holes or cover holes) through which each of the first to ninth driving wires (W11 to W33) pass. The wire cover 14 has a first exposure hole 14*a*11, a second exposure hole 14*a*12, a third exposure hole 14*a*13, a fourth exposure hole 14*a*21, a fifth exposure hole 14*a*22, a sixth exposure hole 14*a*23, a seventh exposure hole 14*a*31, an eighth exposure hole 14*a*32, and a ninth exposure hole 14*a*33. The first to ninth exposure holes (14*a*11 to 14*a*33) correspond to the first to ninth driving wires (W11 to W33), respectively. The numerals following the reference numerals 14*a* indicate the numbers of the corresponding driving wires. For example, the first driving wire W11 is inserted into the first exposure hole 14*a*11.

Any one of the first to ninth exposure holes (14*a*11 to 14*a*33) can be referred to as an exposure hole 14*a*. In the present exemplary embodiment, the first to ninth exposure holes (14*a*11 to 14*a*33) have the same shape.

The wire cover 14 can be moved to the cover position (see FIG. 14A) where the first to ninth driving wires (W11 to W33) are covered and a cover-retracted position (see FIG. 14B) where the wire cover 14 is retracted from the cover position. The cover-retracted position can also be referred to as the exposure position, where the first to ninth driving wires (W11 to W33) are exposed.

Before the catheter unit 100 is attached to the base unit 200, the wire cover 14 is located at the cover position. When the catheter unit 100 is attached to the base unit 200, the wire cover 14 moves from the cover position to the exposure position along the attachment and detachment direction DE.

In the present exemplary embodiment, the wire cover 14 is retained at the exposure position after the movement from the cover position to the exposure position. The wire cover 14 is thus retained at the exposure position if the catheter unit 100 is attached to the base unit 200 and then the catheter unit 100 is detached from the base unit 200.

However, the wire cover 14 may be configured to return to the cover position after the movement from the cover position to the exposure position. For example, the catheter unit 100 may include a biasing member for biasing the wire cover 14 from the exposure position toward the cover position. In such a case, if the catheter unit 100 is attached to the base unit 200 and then the catheter unit 100 is detached from the base unit 200, the wire cover 14 is moved from the exposure position to the cover position.

When the wire cover 14 is at the exposure position, the first to ninth portions to be held (Wa11 to Wa33) of the first to ninth driving wires (W11 to W33) are exposed. As a result, the bending driving unit 13 can be coupled to the coupling device 21 to be described below. When the wire cover 14 is at the exposure position, the first to ninth portions to be held (Wa11 to Wa33) of the first to ninth driving wires (W11 to W33) protrude from the first to ninth exposure holes (14*a*11 to 14*a*33). More specifically, the first to ninth portions to be held (Wa11 to Wa33) protrude from the first to ninth exposure holes (14*a*11 to 14*a*33) in an attachment direction Da to be described below.

As illustrated in FIG. 4B, the first to ninth driving wires (W11 to W33) are arranged along a circle (imaginary circle) having a predetermined radius.

In the present exemplary embodiment, the catheter unit 100 includes a key shaft (key or catheter-side key) 15. In the present exemplary embodiment, the key shaft 15 extends in the attachment and detachment direction DE. The wire cover 14 has a shaft hole 14*b* for the key shaft 15 to pass through. The key shaft 15 can be engaged with a key receptor portion 22 to be described below. The engagement of the key shaft 15 with the key receptor portion 22 limits the movement of the catheter unit 100 with respect to the base unit 200 in the circumferential direction of the circle (imaginary circle) on which the first to ninth driving wires (W11 to W33) are arranged to within a predetermined range.

In the present exemplary embodiment, when seen in the attachment and detachment direction DE, the first to ninth driving wires (W11 to W33) are arranged outside the key shaft 15 to surround the key shaft 15. In other words, the key shaft 15 is located inside the circle (imaginary circle) on which the first to ninth driving wires (W11 to W33) are arranged. The key shaft 15 and the first to ninth driving wires (W11 to W33) can thus be disposed in a space saving manner.

In the present exemplary embodiment, the catheter unit 100 includes the operation unit 400. The operation unit 400 is configured to be movable (rotatable) with respect to the proximal end cover 16 and the bending driving unit 13. The operation unit 400 can rotate about a rotation axis 400*r*. The rotation axis 400*r* of the operation unit 400 extends in the attachment and detachment direction DE.

The operation unit 400 is configured to be movable (rotatable) with respect to the base unit 200 in the state where the catheter unit 100 is attached to the base unit 200. More specifically, the operation unit 400 is configured to be movable (rotatable) with respect to the base housing 200*f*, the wire driving unit 300, and the coupling device 21 to be described below.

<Base Unit>

The base unit 200 and the wire driving unit 300 will be described with reference to FIGS. 5A to 5C.

Figure 5A:
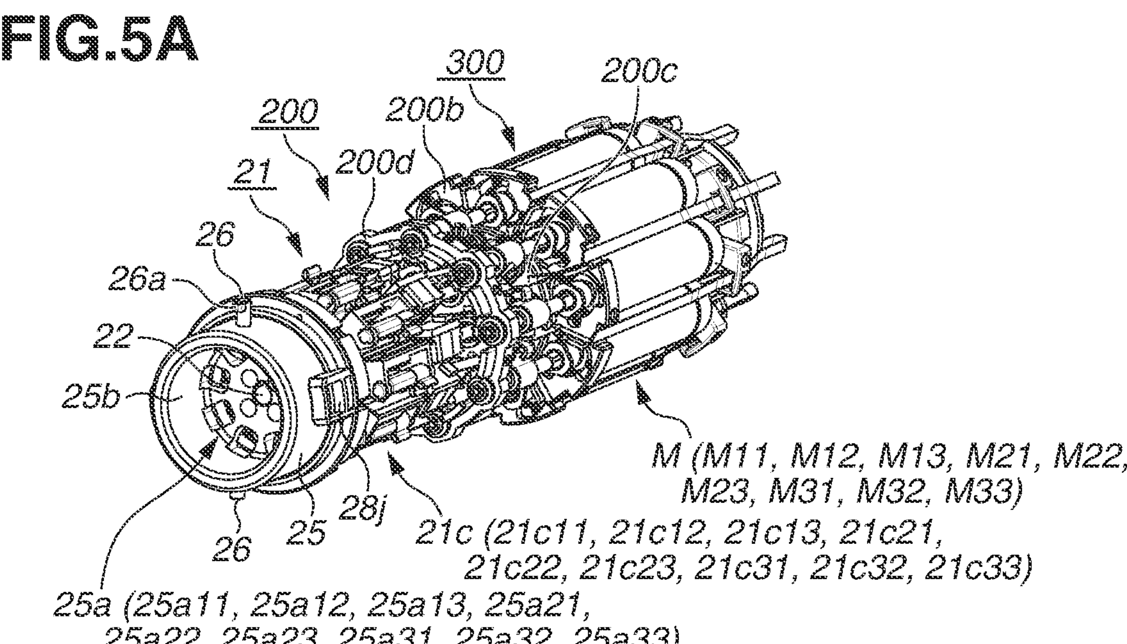
FIG. 5A is an explanatory diagram of a base unit and a wire driving unit.
Figure 5B:
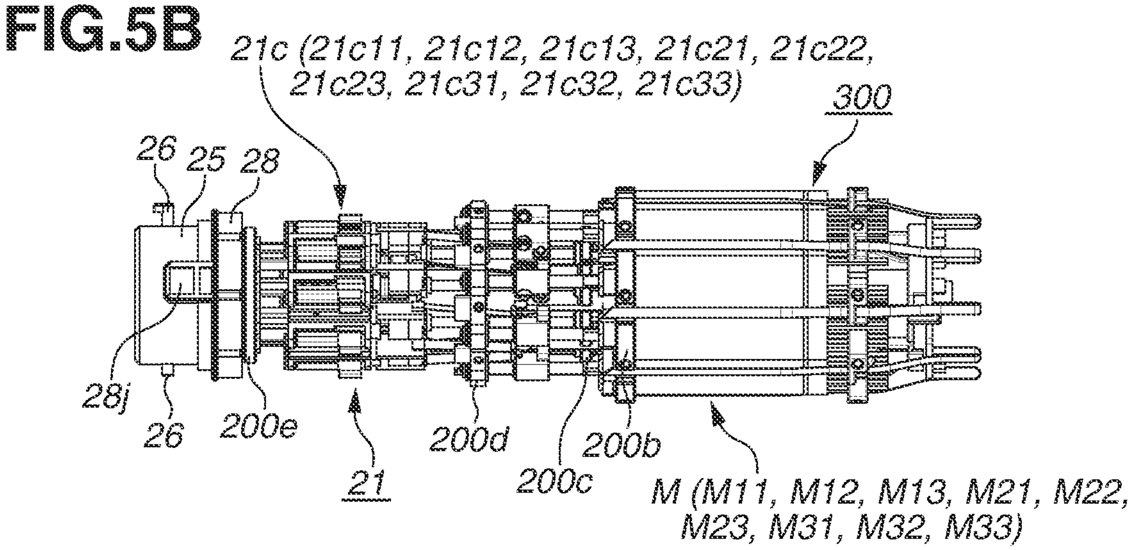
FIG. 5B is an explanatory diagram of the base unit and the wire driving unit.
Figure 5C:
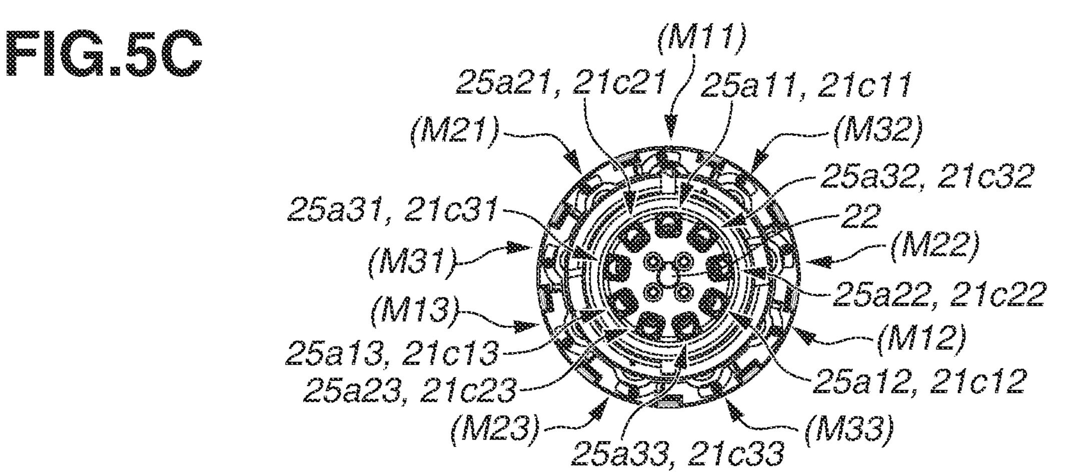
FIG. 5C is an explanatory diagram of the base unit and the wire driving unit.

FIGS. 5A to 5C are explanatory diagrams of the base unit 200 and the wire driving unit 300. FIG. 5A is a perspective view illustrating an internal structure of the base unit 200. FIG. 5B is a side view illustrating the internal structure of the base unit 200. FIG. 5C is a view of the base unit 200 seen along the attachment and detachment direction DE.

As described above, the medical device 1 includes the base unit 200 and the wire driving unit 300. In the present exemplary embodiment, the wire driving unit 300 is accommodated in the base housing 200*f* and located inside the base unit 200. In other words, the base unit 200 includes the wire driving unit 300.

The wire driving unit 300 includes a plurality of driving sources (motors). In the present exemplary embodiment, the wire driving unit 300 includes a first driving source M11, a second driving source M12, a third driving source M13, a fourth driving source M21, a fifth driving source M22, a sixth driving source M23, a seventh driving source M31, an eighth driving source M32, and a ninth driving source M33.

Any one of the first to ninth driving sources (M11 to M33) can be referred to as a driving source M. In the present exemplary embodiment, the first to ninth driving sources (M11 to M33) have the same configuration.

The base unit 200 includes the coupling device 21. The coupling device 21 is accommodated in the base housing 200*f*. The coupling device 21 is connected to the wire driving unit 300. The coupling device 21 includes a plurality of coupling units. In the present exemplary embodiment, the coupling device 21 includes a first coupling unit 21*c*11, a second coupling unit 21*c*12, a third coupling unit 21*c*13, a fourth coupling unit 21*c*21, a fifth coupling unit 21*c*22, a sixth coupling unit 21*c*23, a seventh coupling unit 21*c*31, an eighth coupling unit 21*c*32, and a ninth coupling unit 21*c*33.

Any one of the first to ninth coupling units (21*c*11 to 21*c*33) can be referred to as a coupling unit 21*c*. In the present exemplary embodiment, the first to ninth coupling units (21*c*11 to 21*c*33) have the same configuration.

Each of the plurality of coupling units is connected to each of the plurality of driving sources and driven by each of the plurality of driving sources. Specifically, the first coupling unit 21*c*11 is connected to the first driving source M11 and driven by the first driving source M11. The second coupling unit 21*c*12 is connected to the second driving source M12 and driven by the second driving source M12. The third coupling unit 21*c*13 is connected to the third driving source M13 and driven by the third driving source M13. The fourth coupling unit 21*c*21 is connected to the fourth driving source M21 and driven by the fourth driving source M21. The fifth coupling unit 21*c*22 is connected to the fifth driving source M22 and driven by the fifth driving source M22. The sixth coupling unit 21*c*23 is connected to the sixth driving source M23 and driven by the sixth driving source M23. The seventh coupling unit 21*c*31 is connected to the seventh driving source M31 and driven by the seventh driving source M31. The eighth coupling unit 21*c*32 is connected to the eighth driving source M32 and driven by the eighth driving source M32. The ninth coupling unit 21*c*33 is connected to the ninth driving source M33 and driven by the ninth driving source M33.

As will be described below, the bending driving unit 13 including the first to ninth driving wires (W11 to W33) is coupled to the coupling device 21. The bending driving unit 13 receives driving force of the wire driving unit 300 via the coupling device 21 and bends the bending driving unit 12.

The driving wires W are coupled to the coupling units 21*c* via the portions to be held Wa. Each of the plurality of driving wires is coupled to each of the plurality of coupling units.

Specifically, the first portion to be held Wa11 of the first driving wire W11 is coupled to the first coupling unit 21*c*11. The second portion to be held Wa12 of the second driving wire W12 is coupled to the second coupling unit 21*c*12. The third portion to be held Wa13 of the third driving wire W13 is coupled to the third coupling unit 21*c*13. The fourth portion to be held Wa21 of the fourth driving wire W21 is coupled to the fourth coupling unit 21*c*21. The fifth portion to be held Wa22 of the fifth driving wire W22 is coupled to the fifth coupling unit 21*c*22. The sixth portion to be held Wa23 of the sixth driving wire W23 is coupled to the sixth coupling unit 21*c*23. The seventh portion to be held Wa31 of the seventh driving wire W31 is coupled to the seventh coupling unit 21*c*31. The eighth portion to be held Wa32 of the eighth driving wire W32 is coupled to the eighth coupling unit 21*c*32. The ninth portion to be held Wa33 of the ninth driving wire W33 is coupled to the ninth coupling unit 21*c*33.

The base unit 200 includes a base frame 25. The base frame 25 has a plurality of insertion holes through which each of the first to ninth driving wires (W11 to W33) pass. The base frame 25 has a first insertion hole 25*a*11, a second insertion hole 25*a*12, a third insertion hole 25*a*13, a fourth insertion hole 25*a*21, a fifth insertion hole 25*a*22, a sixth insertion hole 25*a*23, a seventh insertion hole 25*a*31, an eighth insertion hole 25*a*32, and a ninth insertion hole 25*a*33. The first to ninth insertion holes (25*a*11 to 25*a*33) correspond to the first to ninth driving wires (W11 to W33), respectively. The numerals following the reference numerals 25*a* indicate the numbers of the corresponding driving wires. For example, the first driving wire W11 is inserted into the first insertion hole 25*a*11.

Any one of the first to ninth insertion holes (25*a*11 to 25*a*33) can be referred to as an insertion hole 25*a*. In the present exemplary embodiment, the first to ninth insertion holes (25*a*11 to 25*a*33) have the same shape.

The base frame 25 has an attachment opening 25*b* into which the wire cover 14 is inserted. The first to ninth insertion holes (25*a*11 to 25*a*33) are located in the bottom of the attachment opening 25*b*.

The base unit 200 further includes a motor frame 200*b*, a first bearing frame 200*c*, a second bearing fame 200*d*, and a third bearing frame 200*e*. The motor frame 200*b*, the first bearing frame 200*c*, the second bearing frame 200*d*, and the third bearing frame 200*e* are coupled to each other.

The base frame 25 includes the key receptor portion (key hole, base-side key, or main body-side key) 22 that accepts the key shaft 15. The engagement between the key shaft 15 and the key receptor portion 22 prevents the catheter unit 100 from being attached to the base unit 200 in a wrong phase.

The engagement between the key shaft 15 and the key receptor portion 22 limits the movement of the catheter unit 100 with respect to the base unit 200 in the circumferential direction of the circle (imaginary circle) on which the first to ninth driving wires (W11 to W33) are arranged to within the predetermined range.

As a result, the first to driving wires (W11 to W33) are engaged with the respective corresponding first to ninth insertion holes (25*a*11 to 25*a*33) and the respective corresponding first to ninth coupling units (21*c*11 to 21*c*33). In other words, the driving wires W are prevented from being engaged with insertion holes 25*a* different from the corresponding insertion holes 25*a* or the coupling units 21*c* different from the corresponding coupling units 21*c*.

The user can properly couple the first to ninth driving wires (W11 to W33) to the first to ninth coupling units (21*c*11 to 21*c*33), respectively, by engaging the key shaft 15 with the key receptor portion 22. The user can thus easily attach the catheter unit 100 to the base unit 200.

In the present exemplary embodiment, the key shaft 15 includes a protrusion protruding in a direction intersecting the attachment and detachment direction DE. The key receptor portion 22 has a recess for the protrusion to be inserted into. The circumferential position where the protrusion and the recess are engaged with each other is the position where the driving wires W are engaged with the corresponding insertion holes 25*a* and the corresponding coupling units 21*c*.

The key shaft 15 can be disposed on either the base unit 200 or the catheter unit 100, and the key receptor portion 22 in the other. For example, the key shaft 15 may be disposed on the base unit 200, and the key receptor portion 22 in the catheter unit 100.

The base unit 200 includes a joint 28 including joint engagement portions 28*j*. The base frame 25 includes a lock shaft 26 including a lock protrusion 26*a*. The functions of these members will be described below.

<Coupling Between Motors and Driving Wires>

Figure 6A:
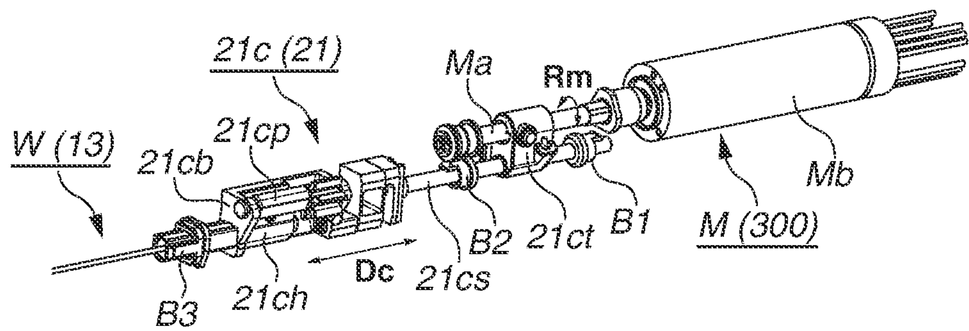
FIG. 6A is an explanatory diagram of the wire driving unit, a coupling device, and a bending driving unit.
Figure 6B:
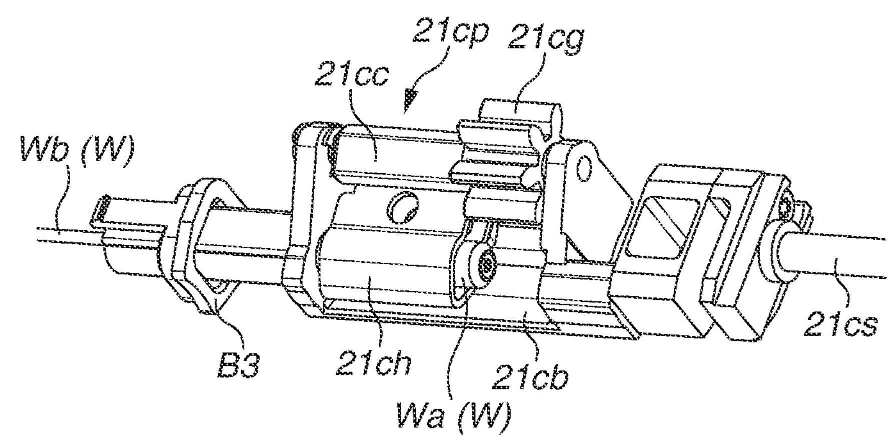
FIG. 6B is an explanatory diagram of the wire driving unit, the coupling device, and the bending driving unit.
Figure 6C:
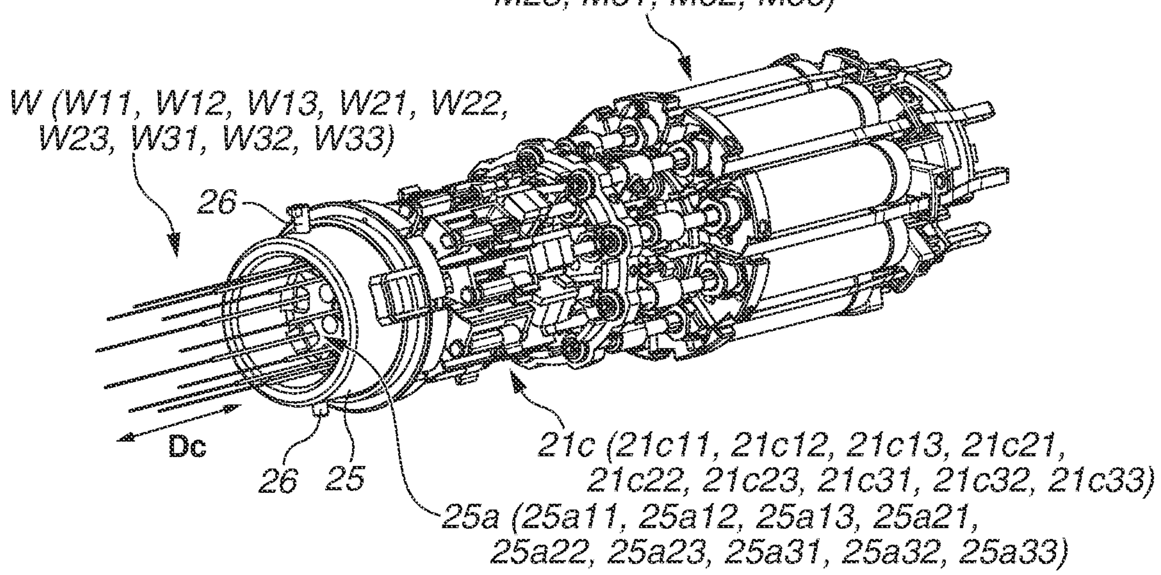
FIG. 6C is an explanatory diagram of the wire driving unit, the coupling device, and the bending driving unit.

The coupling between the wire driving unit 300, the coupling device 21, and the bending driving unit 13 will be determined with reference to FIGS. 6A to 6C.

FIGS. 6A to 6C are explanatory diagrams of the wire driving unit 300, the coupling device 21, and the bending driving unit 13. FIG. 6A is a perspective view of a driving source M, a coupling unit 21*c*, and a driving wire W. FIG. 6B is an enlarged view of the coupling unit 21*c* and the driving wire W. FIG. 6C is a perspective illustrating the coupling between the wire driving unit 300, the coupling device 21, and the bending driving unit 13.

In the present exemplary embodiment, the first to ninth driving wires (W11 to W33) and the first to ninth coupling units (21*c*11 to 21*c*33) are coupled by the respective same configurations. The first to ninth coupling units (21*c*11 to 21*c*33) and the first to ninth driving sources (M11 to M33) are connected by the respective same configurations. In the following description, the connecting configurations will therefore be described by using one driving wire W, one coupling unit 21*c*, and one driving source M.

As illustrated in FIG. 6A, the driving source M includes an output shaft Ma and a motor main body Mb that rotates the output shaft Ma in a direction of rotation Rm. A helical groove is formed in the surface of the output shaft Ma. The output shaft Ma has a so-called screw shape. The motor main body Mb is fixed to the motor frame 200*b*.

The coupling unit 21*c* includes a tractor 21*ct* connected to the output shaft Ma and a tractor support shaft 21*cs* supporting the tractor 21*ct*. The tractor support shaft 21*cs* is connected to a coupling base 21*cb*.

The coupling unit 21*c* includes a plate spring 21*ch* serving as a holding unit for holding the portion to be held Wa of the driving wire W. The driving wire W passes through the insertion hole 25*a* and is engaged with the coupling unit 21*c*. More specifically, the portion to be held Wa is engaged with the plate spring 21*ch*. As will be described below, the plate spring 21*ch* can take a state of pinching and fixing the portion to be held Wa (fixed state) and a state of releasing the portion to be held Wa (released state).

The coupling unit 21*c* includes a pressing member 21*cp*. The pressing member 21*cp* includes a gear portion 21*cg* to mesh with an internal gear 29 to be described below, and a cam 21*cc* serving as a pressing portion for pressing the plate spring 21*ch*.

As will be described below, the cam 21*cc* can move with respect to the plate spring 21*ch*. The movement of the cam 21*cc* switches the fixed state and the released state of the plate spring 21*ch*.

The coupling unit 21*c* is supported by a first bearing B1, a second bearing B2, and a third bearing B3. The first bearing B1 is supported by the first bearing frame 200*c* of the base unit 200. The second bearing B2 is supported by the second bearing frame 200*d* of the base unit 200. The third bearing B3 is supported by the third bearing frame 200*e* of the base unit 200. The rotation of the coupling unit 21*c* about the motor shaft Ma is thus restricted when the motor shaft Ma rotates in the direction of rotation Rm. The first bearing B1, the second bearing B2, and the third bearing B3 are provided for each of the first to ninth coupling units (21*c*11 to 21*c*33).

Since the rotation of the coupling unit 21*c* about the motor shaft Ma is restricted, the helical groove of the motor shaft Ma produces force along the direction of the rotation axis of the motor shaft Ma on the tractor 21*ct* as the motor shaft Ma rotates. As a result, the coupling unit 21*c* moves along the direction of the rotation axis of the motor shaft Ma (direction Dc). The movement of the coupling unit 21*c* moves the driving wire W and bends the bending unit 12.

In other words, the motor shaft Ma and the tractor 21*ct* constitute a so-called feed screw, which threadedly converts the rotational motion transmitted from the driving source M into linear motion. In the present exemplary embodiment, the motor shaft Ma and the tractor 21*ct* constitute a slide screw, whereas a ball screw may be employed.

As illustrated in FIG. 6C, the first to ninth driving wires (W11 to W33) and the first to ninth coupling units (21*c*11 to 21*c*33) are respectively coupled to each other by the attachment of the catheter unit 100 to the base unit 200.

The control unit 3 can control the first to ninth driving sources (M11 to M33) independent of each other. More specifically, any given one of the first to ninth driving sources (M11 to M33) can be independently operated or stopped regardless of whether the other driving sources are at rest. In other words, the control unit 3 can control the first to ninth driving wires (W11 to W33) independent of each other. As a result, the first to third guide rings (J1 to J3) are controlled independent of each other, and the bending region 12*b* of the bending unit 12 can be bent in any given direction.

<Attachment of Catheter Unit>

An operation for attaching the catheter unit 100 to the base unit 200 will be described with reference to FIGS. 7A and 7B.

Figure 7A:
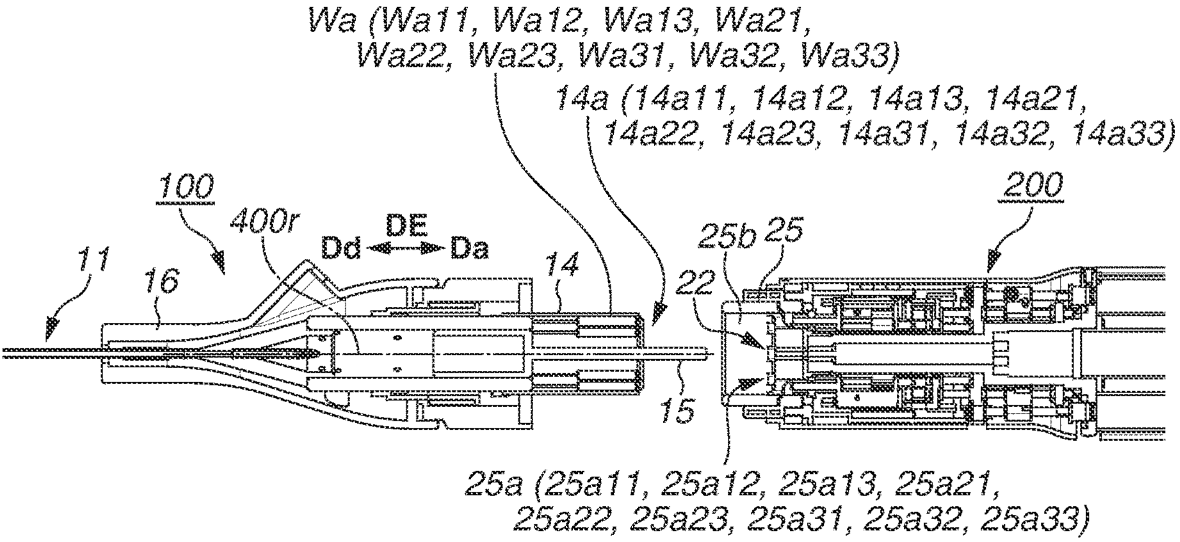
FIG. 7A is an explanatory diagram of attachment of the catheter unit.
Figure 7B:
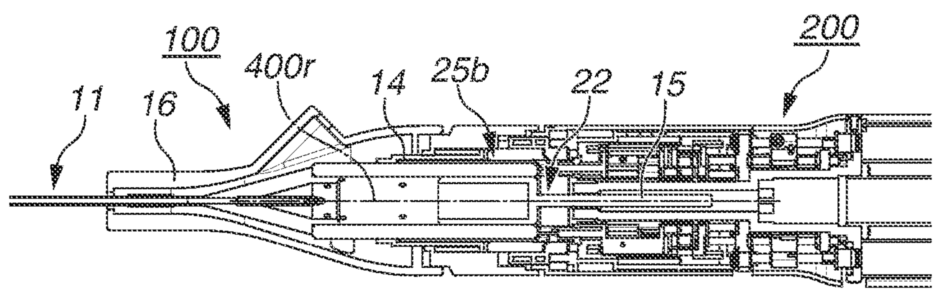
FIG. 7B is an explanatory diagram of the attachment of the catheter unit.

FIGS. 7A and 7B are explanatory diagrams of the attachment of the catheter unit 100. FIG. 7A is a diagram before the catheter unit 100 is attached to the base unit 200. FIG. 7B is a diagram after the catheter unit 100 is attached to the base unit 200.

In the present exemplary embodiment, the attachment and detachment direction DE of the catheter unit 100 is the same as the direction of the rotation axis 400*r* of the operation unit 400. A direction along the attachment and detachment direction DE in which the catheter unit 100 is attached to the base unit 200 will be referred to as an attachment direction Da. A direction along the attachment and detachment direction DE in which the catheter unit 100 is detached from the base unit 200 (direction opposite the attachment direction Da) will be referred to as a detachment direction Dd.

As illustrated in FIG. 7A, in the state before the catheter unit 100 is attached to the base unit 200, the wire cover 14 is located at the cover position. Here, the wire cover 14 covers the first to ninth driving wires (W11 to W33) so that the first to ninth portions to be held (Wa11 to Wa33) do not protrude from the first to ninth exposure holes (14*a*11 to 14*a*33) of the wire cover 14. The first to ninth driving wires (W11 to W33) can thus be protected in the state before the catheter unit 100 is attached to the base unit 200.

When the catheter unit 100 attaches the base unit 200, the key shaft 15 is engaged with the key receptor portion 22. The key shaft 15 protrudes from the wire cover 14. In the present exemplary embodiment, the wire cover 14 is not engaged with the attachment opening 25*b* in the state where the key shaft 15 has reached the inlet of the key receptor portion 22. In other words, if the phase of the catheter unit 100 with respect to the base unit 200 is such that the key shaft 15 and the key receptor portion 22 are unable to be engaged with each other, the wire cover 14 is not engaged with the attachment opening 25*b* but maintained at the cover position. The first to the ninth driving wires (W11 to W33) are therefore protected even if the catheter unit 100 is moved to engage the key shaft 15 and the key receptor portion 22 with each other.

If the key shaft 15 and the key receptor portion 22 are engaged with each other and the catheter unit 100 is moved in the attachment direction Da with respect to the base unit 200, the catheter unit 100 is attached to the base unit 200. The attachment of the catheter unit 100 to the base unit 200 moves the wire cover 14 to the exposure position. In the present exemplary embodiment, the wire cover 14 makes contact with the base frame 25 and thereby moves from the cover position to the exposure position (see FIG. 7B).

More specifically, in attaching the catheter unit 100, the wire cover 14 comes into contact with the base frame 25 and stops. If the catheter unit 100 is moved in the attachment direction Da in such a state, the wire cover 14 moves relative to the portions other than the wire cover 14 in the catheter unit 100. As a result, the wire cover 14 moves from the cover position to the exposure position.

While the wire cover 14 moves from the cover position to the exposure position, the portions to be held Wa of the driving wires W protrude from the exposure holes 14*a* of the wire cover 14 and are inserted into the insertion holes 25*a*. The portions to be held Wa are then engaged with the plate springs 21*ch* of the coupling units 21*c* (see FIG. 6B).

In the state where the catheter unit 100 is simply attached to the base unit 200, the catheter unit 100 can be moved in the detachment direction Dd with respect to the base unit 200 and detached. As will be described below, the state where the catheter unit 100 is simply attached to the base unit 200 is where the driving wires W and the coupling units 21*c* are unfixed.

Detachment of the catheter unit 100 from the base unit 200 is prevented by operating the operation unit 400 in the state where the catheter unit 100 is attached to the base unit 200. Moreover, by operating the operation unit 400 in the state where the catheter unit 100 is attached to the base unit 200, the bending driving unit 13 is fixed to the coupling device 21 and the bending driving unit 13 is coupled to the wire driving unit 300 via the coupling device 21.

<Fixing and Unfixing of Bending Driving Unit>

A configuration for fixing the bending driving unit 13 to the coupling device 21 and a configuration for unfixing the bending driving unit 13 from the coupling device 21 will be described with reference to FIGS. 8A, 8B, 9, 10, 11, 12, 13, and 14.

Figure 8A:
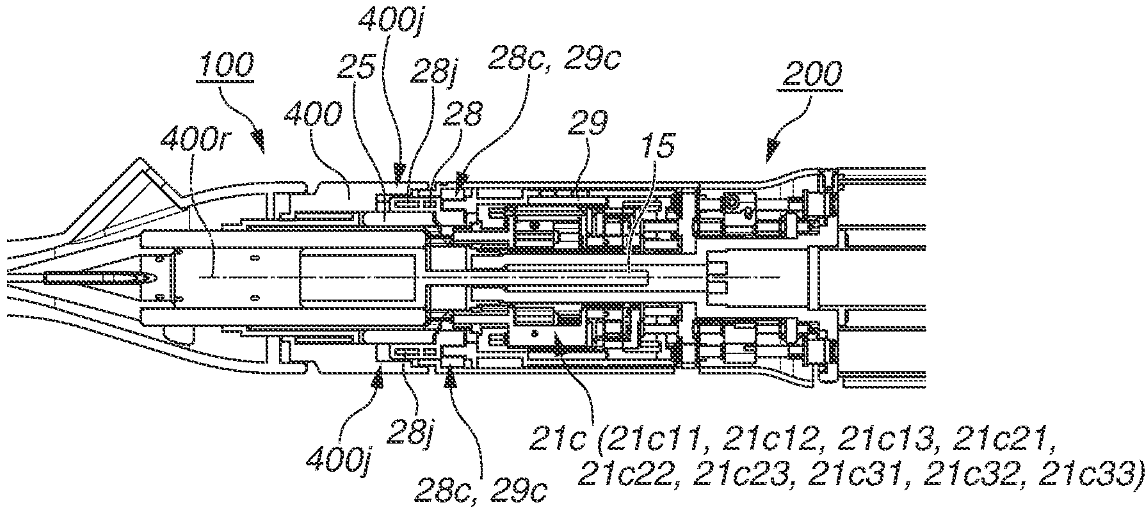
FIG. 8A is a diagram for describing coupling between the catheter unit and the base unit.
Figure 8B:
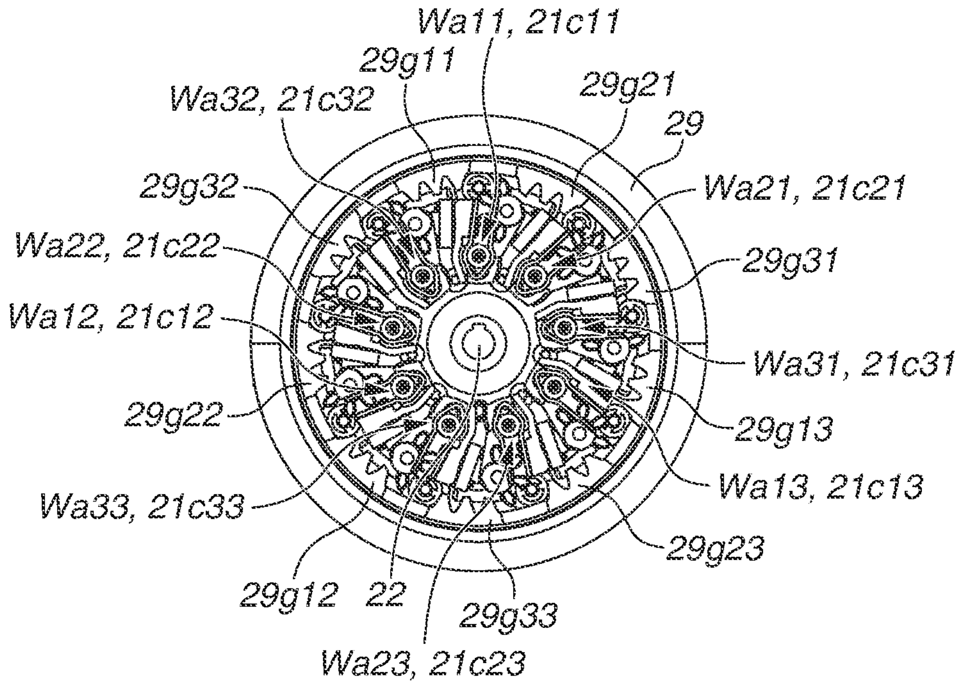
FIG. 8B is a diagram for describing the coupling between the catheter unit and the base unit.

FIGS. 8A and 8B are diagrams for describing the coupling between the catheter unit 100 and the base unit 200. FIG. 8A is a sectional view of the catheter unit 100 and the base unit 200. FIG. 8A is a sectional view of the catheter unit 100 and the base unit 200, taken along the rotation axis 400*r*. FIG. 8B is a sectional view of the base unit 200. FIG. 8B is a sectional view of the base unit 200 in a portion where the coupling units 21*c* are, taken in a direction orthogonal to the rotation axis 400*r*.

Figure 9:
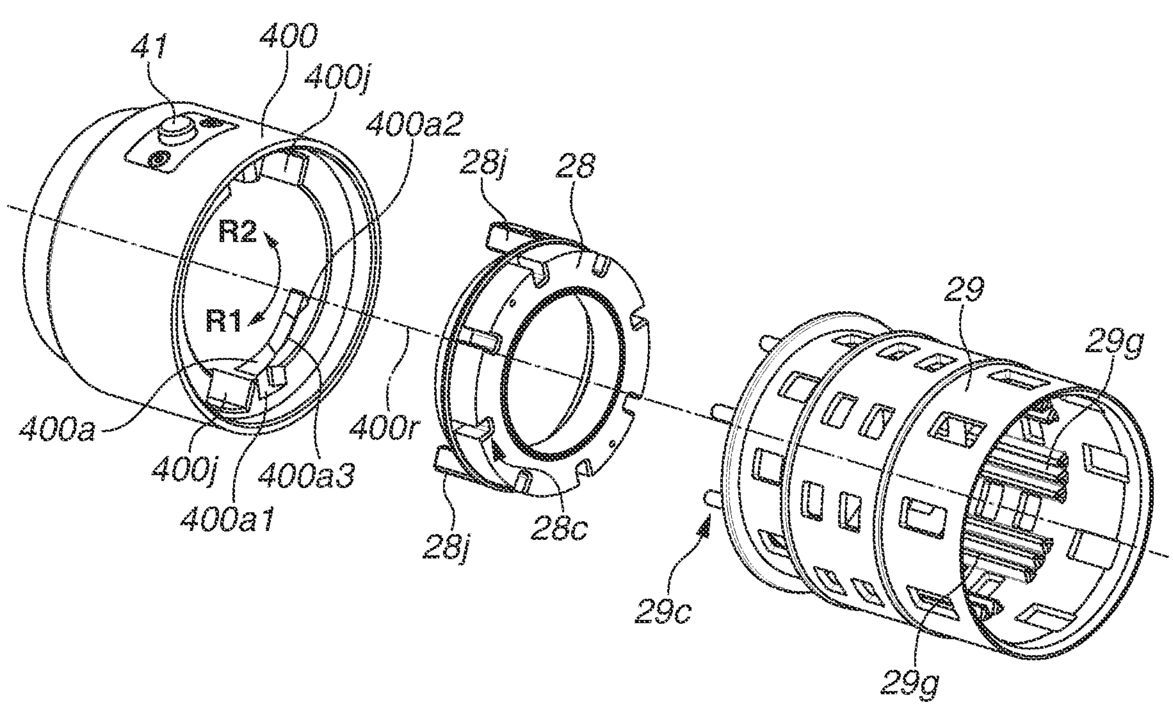
FIG. 9 is an exploded view for describing the coupling between the catheter unit and the base unit.

FIG. 9 is an exploded view for describing the coupling between the catheter unit 100 and the base unit 200.

FIGS. 10, 11, 12, 13, and 14 are diagrams for describing the fixing of the driving wires W by the coupling units 21*c*.

As illustrated in FIGS. 8A and 9, the base unit 200 includes the joint (intermediate member or second transmission member) 28, and the internal gear 29 serving as a moving gear (interlocking gear, transmission member, or first transmission member) interlocked with the operation unit 400 via the joint 28.

The joint 28 includes a plurality of transmission portions 28*c*. The internal gear 29 includes a plurality of portions to be transmitted 29*c*. The plurality of transmission portions 28*c* is engaged with the plurality of transmission portions 29*c*. If the joint 28 rotates, the rotation of the joint 28 is transmitted to the internal gear 29.

If the catheter unit 100 is attached to the base unit 200, engagement portions 400*j* of the operation unit 400 are engaged with the joint engagement portions 28*j* of the joint 28. If the operation unit 400 is rotated, the rotation of the operation unit 400 is transmitted to the joint 28. The operation unit 400, the joint 28, and the internal gear 29 rotate in the same direction.

The internal gear 29 includes a plurality of tooth portions for the first to ninth coupling units (21*c*11 to 21*c*33) to switch between a state of fixing the respective first to ninth driving wires (W11 to W33) and a state of releasing the respective first to ninth driving wires (W11 to W33). Each of the plurality of tooth portions (action portions or switching gear portions) of the internal gear 29 is engaged with gear portions 21*cg* of the pressing members 21*cp* of the respective first to ninth coupling units (21*c*11 to 21*c*33).

Specifically, in the present exemplary embodiment, the internal gear 29 includes a first tooth portion 29*g*11, a second tooth portion 29*g*12, a third tooth portion 29*g*13, a fourth tooth portion 29*g*21, a fifth tooth portion 29*g*22, a sixth tooth portion 29*g*23, a seventh tooth portion 29*g*31, an eighth tooth portion 29*g*32, and a ninth tooth portion 29*g*33. The first to ninth tooth portions (29*g*11 to 29*g*33) are formed with some gap between each other.

The first tooth portion 29*g*11 meshes with the gear portion 21*cg* of the first coupling unit 21*c*11. The second tooth portion 29*g*12 meshes with the gear portion 21*cg* of the second coupling unit 21*c*12. The third tooth portion 29*g*13 meshes with the gear portion 21*cg* of the third coupling unit 21*c*13. The fourth tooth portion 29*g*21 meshes with the gear portion 21*cg* of the fourth coupling unit 21*c*21. The fifth tooth portion 29*g*22 meshes with the gear portion 21*cg* of the fifth coupling unit 21*c*22. The sixth tooth portion 29*g*23 meshes with the gear portion 21*cg* of the sixth coupling unit 21*c*23. The seventh tooth portion 29*g*31 meshes with the gear portion 21*cg* of the seventh coupling unit 21*c*31. The eighth tooth portion 29*g*32 meshes with the gear portion 21*cg* of the eighth coupling unit 21*c*32. The ninth tooth portion 29*g*33 meshes with the gear portion 21*cg* of the ninth coupling unit 21*c*33.

Any one of the first to ninth tooth portions (29*g*11 to 29*g*33) can be referred to as a tooth portion 29*g*. In the present exemplary embodiment, the first to ninth tooth portions (29*g*11 to 29*g*33) have the same configuration.

In the present exemplary embodiment, the first to ninth driving wires (W11 to W33) and the first to ninth coupling units (21*c*11 to 21*c*33) are coupled by the respective same configurations. The first to ninth coupling units (21*c*11 to 21*c*33) and the first to ninth tooth portions (29*g*11 to 29*g*33) are connected by the respective same configurations. In the following description, such connecting configurations will therefore be described by using one driving wire W, one coupling unit 21*c*, and one tooth portion 29*g*.

In each of the first to ninth coupling units (21*c*11 to 21*c*33), the gear portion 21*cg* is moved by the internal gear 29, whereby the pressing member 21*cp* is rotated to move the cam 21*cc* between a pressing position and a retracted position where the cam 21*cc* is retracted from the pressing position.

Rotating the operation unit 400 rotates the internal gear 29. The rotation of the internal gear 29 operates each of the first to ninth coupling units (21*c*11 to 21*c*33). In other words, the first to ninth coupling units (21*c*11 to 21*c*33) can be operated by the operation of rotating a single operation unit 400.

The operation unit 400 can move between a fixed position (locked position) and a detachment position in the state where the catheter unit 100 is attached to the base unit 200. As will be described below, the operation unit 400 can move to an unlocked position in the state where the catheter unit 100 is attached to the base unit 200. The unlocked position is located between the fixed position and the detachment position in the circumferential direction of the operation unit 400. The catheter unit 100 is attached to the base unit 200 with the operation unit 400 located at the detachment position.

The state where the catheter unit 100 is attached to the base unit 200 is where the driving wire W is unfixed (unlocked) from the coupling unit 21*c*. Such a state will be referred to as an unlocked state of the coupling unit 21*c*. The state where the driving wire W is fixed (locked) to the coupling unit 21*c* will be referred to as a locked state of the coupling unit 21*c*.

The operation in fixing the driving wire W to the coupling unit 21*c* will be described with reference to FIGS. 10, 11, 12, 13, and 14.

After the catheter unit 100 is attached to the base unit 200 and before the operation unit 400 is operated, the catheter unit 100 can be detached from the base unit 200. The state where the catheter unit 100 can be detached from the base unit 200 will hereinafter be referred to as a detachable state.

Figure 10:
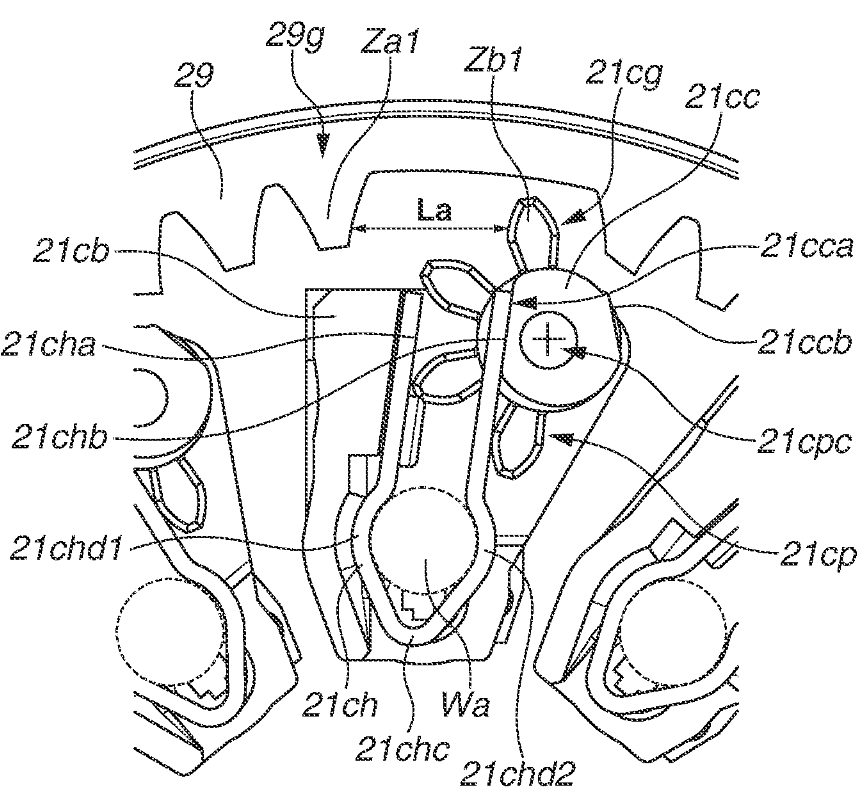
FIG. 10 is a diagram for describing fixing of driving wires by coupling units.

FIG. 10 is a diagram illustrating the state of the internal gear 29 and the coupling unit 21*c* in the detachable state. FIG. 10 is a diagram illustrating the internal gear 29 and the coupling unit 21*c* in a state where the operation unit 400 is located at the fixed position.

The plate spring 21*ch* of the coupling unit 21*c* includes a portion to be fixed 21*cha* that is fixed to the coupling base 21*cb*, and a portion to be pressed 21*chb* that makes contact with the cam 21*cc* of the pressing member 21*cp*. The plate spring 21*ch* includes a first portion 21*chd*1 and a second portion 21*chd*2. When the catheter unit 100 is attached to the base unit 200, the portion to be held Wa is inserted into between the first portion 21*chd*1 and the second portion 21*chd*2.

The cam 21*cc* includes a holding surface 21*cca* and a pressing surface 21*ccb*. In terms of the radial direction of rotation of the pressing member 21*cp*, the holding surface 21*cca* is located closer to a center of rotation 21*cpc* of the pressing member 21*cp* than the pressing surface 21*ccb*.

As illustrated in FIG. 10, in the detachable state (state where the operation unit 00 is at the detachment position), the plate spring 21*ch* is held at a position where the portion to be pressed 21*chb* is in contact with the holding surface 21*cca*. A tooth Za1 of the internal gear 29 and a tooth Zb1 of the gear portion 21*cg* are stopped with a clearance La therebetween.

The direction of rotation of the operation unit 400 in which the operation unit 400 moves from the detachment position to the unlocked position and the fixed position will be referred to as a locking direction (fixing direction). The direction of rotation in which the operation unit 400 moves from the fixed position to the unlocked position and the detachment position will be referred to as an unlocking direction. The operation unit 400 moves to the detachment position by rotating in the unlocking direction from the unlocked position. The operation unit 400 moves to the fixed position by rotating in the locking direction from the unlocked position.

In the state where the catheter unit 100 is attached to the base unit 200 and the operation unit 400 is at the detachment position, the coupling unit 21*c* is in the unlocked state and the driving wire W is unfixed from the coupling unit 21*c*.

When the coupling unit 21*c* is in the unlocked state, the cam 21*cc* is located at the retracted position where the cam 21*cc* is retracted from the pressing position to be described below. In such a state, the portion to be held Wa is unfixed from the plate spring 21*ch*. The force at which the portion to be held Wa is fastened by the first portion 21*chd*1 and the second portion 21*chd*2 when the coupling unit 21*c* is in the unlocked state is less that at which the portion to be held Wa is fastened by the first portion 21*chd*1 and the second portion 21*chd*2 when the coupling unit 21*c* is in the locked state.

If the catheter unit is moved in the detachment direction Dd with respect to the base unit 200 when the coupling unit 21*c* is in the unlocked state, the portion to be held Wa can be withdrawn from between the first portion 21*chd*1 and the second portion 21*chd*2.

When the coupling unit 21*c* is in the unlocked state, the first portion 21*chd*1 and the second portion 21*chd*2 are desirably in a state of not producing any force (state of producing zero force) to fasten the portion to be held Wa. When the coupling unit 21*c* is in the unlocked state, there is desirably a gap between at least either one of the first and second portions 21*chd*1 and 21*chd*2 and the portion to be held Wa.

Figure 11:
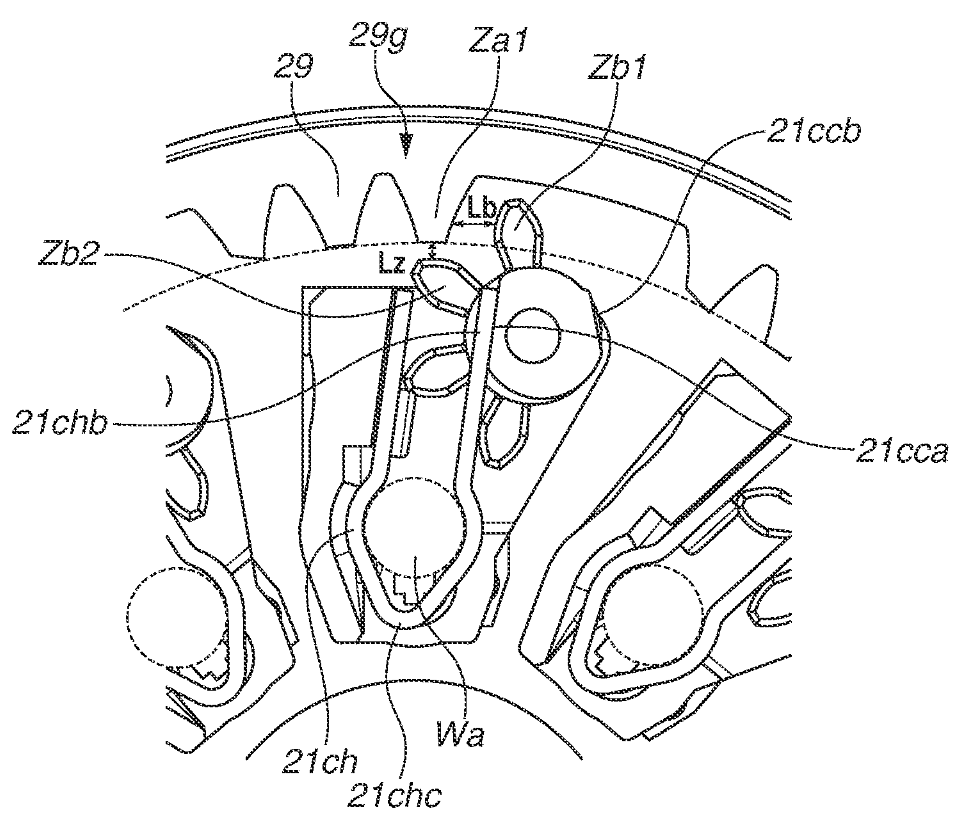
FIG. 11 is a diagram for describing the fixing of the driving wires by the coupling units.

FIG. 11 is a diagram illustrating the state of the internal gear 29 and the coupling unit 21*c* when the operation unit 400 is rotated in the locking direction from the detachment position. FIG. 11 is a diagram illustrating the state of the internal gear 29 and the coupling unit 21*c* in the state where the operation unit 400 is at the unlocked position.

If the operation unit 400 is at the detachment position (FIG. 10) and rotated in the locking direction, the internal gear 29 rotates clockwise. The operation unit 400 is then located at the unlocked position.

Even if the operation unit 400 is rotated, the engagement between the key shaft 15 and the key receptor portion 22 restricts the rotation of the entire catheter unit 100 (excluding the operation unit 400) with respect to the base unit 200. In other words, the operation unit 400 can be rotated with respect to the entire catheter unit 100 (excluding the operation unit 400) and the base unit 200 in a state where the entire catheter unit 100 (excluding the operation unit 400) and the base unit 200 are stationary.

The clockwise rotation of the internal gear 29 reduces the clearance between the tooth Za1 of the internal gear 29 and the tooth Zb1 of the gear portion 21*cg* from the clearance La to a clearance Lb.

A tooth Zb2 of the gear portion 21*cg* is located a clearance Lz away from the tip circle (dotted line) of the tooth portion 29*g* of the internal gear 29. The internal gear 29 can thus rotate without interfering the tooth Zb2. Meanwhile, the coupling unit 21*c* is maintained in the same state as that illustrated in FIG. 10 (unlocked state).

Figure 12:
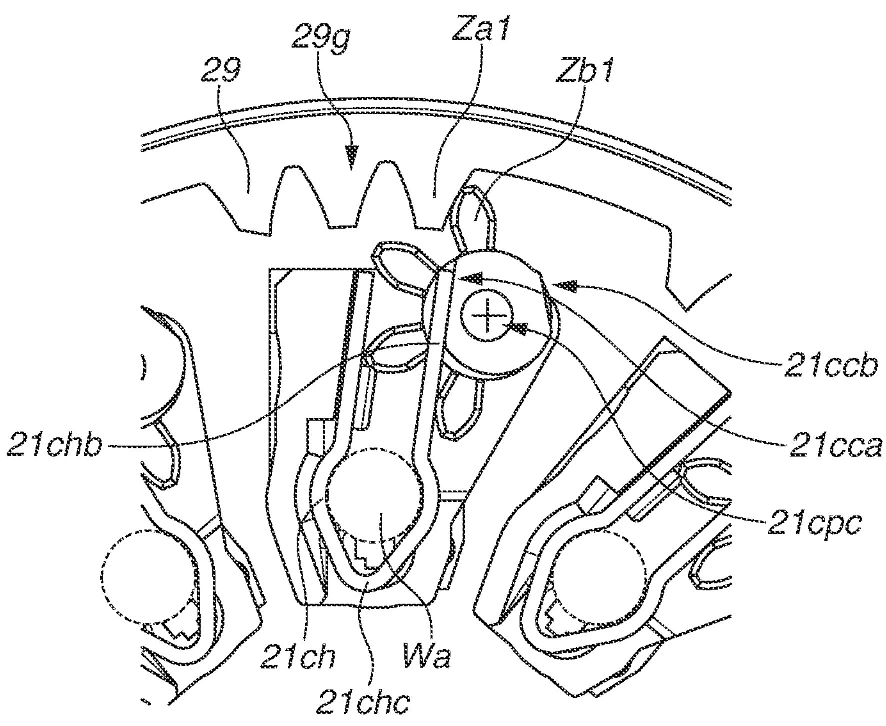
FIG. 12 is a diagram for describing the fixing of the driving wires by the coupling units.

If the operation unit 400 is further rotated in the locking direction from the state illustrated in FIG. 11, the internal gear 29 further rotates clockwise. FIG. 12 illustrates the state of the internal gear 29 and the coupling unit 21*c* here.

FIG. 12 is a diagram illustrating the state of the internal gear 29 and the coupling unit 21*c* when the operation unit 400 is rotated in the locking direction from the unlocked position.

As illustrated in FIG. 12, if the operation unit 400 is rotated in the locking direction from the unlocked position, the tooth Za1 of the internal gear 29 and the tooth Zb1 of the gear portion 21*cg* make contact with each other. Meanwhile, the coupling unit 21*c* is in the same state as illustrated in FIGS. 10 and 11 and maintained in the unlocked state.

Figure 13:
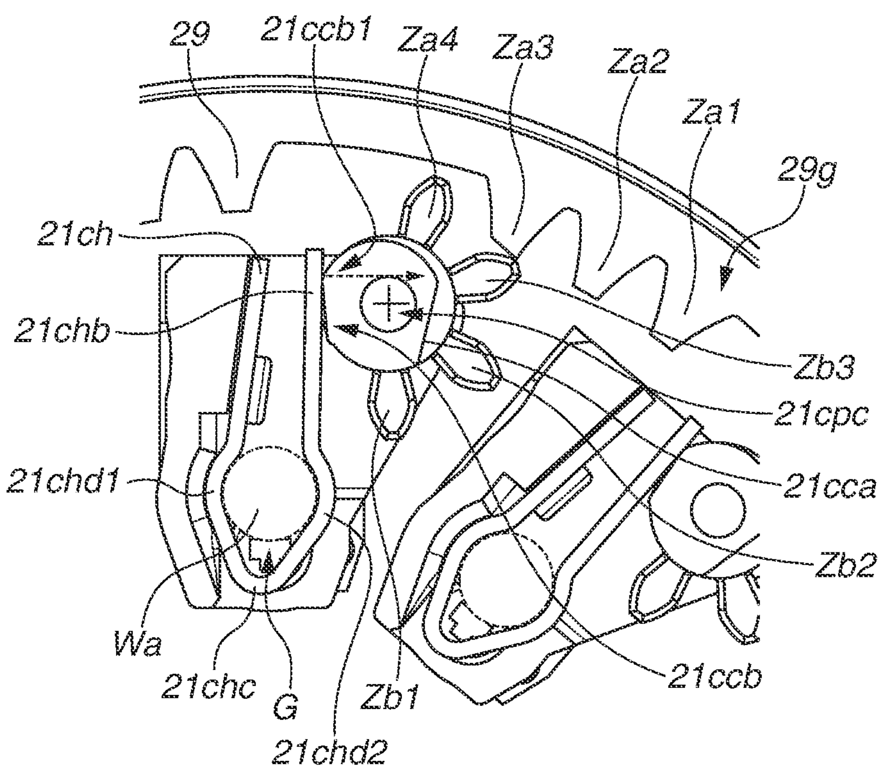
FIG. 13 is a diagram for describing the fixing of the driving wires by the coupling units.

FIG. 13 is a diagram illustrating a state where the pressing member 21*cp* is rotated by rotating the operation unit 400 in the locking direction.

As illustrated in FIG. 13, if the operation unit 400 is further rotated in the locking direction from the state of FIG. 12, the internal gear 29 further rotates clockwise.

As the internal gear 29 moves from the state of FIG. 12 to the state of FIG. 13, the internal gear 29 rotates the gear portion 21*cg* clockwise. The rotation of the gear portion 21*cg* separates the holding surface 21*cca* from the portion to be pressed 21*chb*, and the pressing surface 21*ccb* approaches the portion to be pressed 21*chb*. The first portion 21*chd*1 and the second portion 21*chd*2 then start to pinch the portion to be held Wa.

The portion to be pressed 21*chb* is then pressed by a corner portion 21*ccb*1 located at an end of the pressing surface 21*ccb* while a tooth Za3 of the internal gear 29 moves to a position away from a tooth Zb3 of the gear portion 21*cg*. In such a state, the portion to be held Wa is pinched between the first portion 21*chd*1 and the second portion 21*chd*2.

When the tooth Za3 of the internal gear 29 is separated from the tooth Zb3 of the gear portion 21*cg*, the transmission of the driving force from the internal gear 29 to the gear portion 21*cg* ends. Here, the cam 21*cc* is in a state such that the corner portion 21*ccb*1 receives reaction force from the plate spring 21*ch*.

In the radial direction of rotation of the pressing member 21*cp*, the reaction force of the plate spring 21*ch* acting on the corner portion 21*ccb*1 acts at the position away from the center of rotation 21*cpc* of the pressing member 21*cp*, and the pressing member 21*cp* rotates clockwise. Here, the pressing member 21*cp* rotates in the same direction as that in which the pressing member 21*cp* is rotated by the internal gear 29 rotating clockwise.

Figure 14:
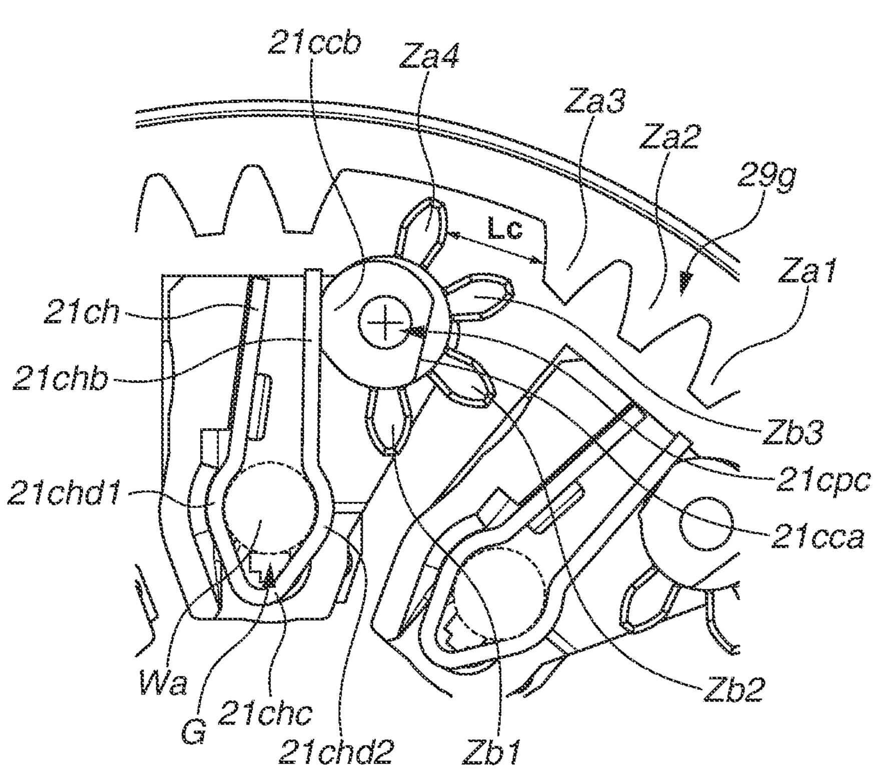
FIG. 14 is a diagram for describing the fixing of the driving wires by the coupling units.

FIG. 14 is a diagram illustrating the state of the internal gear 29 and the coupling unit 21*c* in the state where the operation unit 400 is at the fixed position.

As illustrated in FIG. 14, the pressing member 21*cp* receives the reaction force from the plate spring 21*ch* and rotates further from the state illustrated in FIG. 13.

As illustrated in FIG. 14, the pressing member 21*cp* stops with the pressing surface 21*ccb* of the cam 21*cc* and the portion to be pressed 21*chb* of the plate spring 21*ch* in surface contact with each other. In other words, the pressing surface 21*ccb* and the surface of the portion to be pressed 21*chb* are arranged on the same plane.

Here, the coupling unit 21*c* is in the locked state. When the coupling unit 21*c* is in the locked state, the cam portion 21*cc* of the pressing member 21*cp* is located at the pressing position, and the pressing surface 21*ccb* presses the portion to be pressed 21*chb*.

When the coupling unit 21*c* is in the locked state, the portion to be held Wa is pinched between the first portion 21*chd*1 and the second portion 21*chd*2. In other words, the plate spring 21*ch* is pressed by the cam 21*cc*, and the portion to be held Wa is fastened by the plate spring 21*ch*. As a result, the portion to be held Wa is fixed by the plate spring 21*ch*.

In the present exemplary embodiment, the first portion 21*chd*1 and the second portion 21*chd*2 of the plate spring 21*ch* press the portion to be held Wa at respective separate positions. Moreover, a curbed portion 21*chc* connecting the first portion 21*chd*1 and the second portion 21*chd*2 is located between the first portion 21*chd*1 and the second portion 21*chd*2. The curved portion 21*chc* is located at a gap G from the portion to be held Wa. The first portion 21*chd*1 and the second portion 21*chd*2 can thus stably fix the portion to be held Wa.

The plate spring 21*ch* may be made of a resin or metal material. Metal is desirably used.

When the coupling unit 21*c* is in the locked state, the withdrawal of the portion to be held Wa from between the first portion 21*chd*1 and the second portion 21*chd*2 is restricted.

The tooth Za3 of the internal gear 29 and a tooth Zb4 of the gear portion 21*cg* are stopped at positions with a clearance Lc therebetween.

In unfixing the driving wire W and the coupling unit 21*c*, the operation unit 400 located at the fixed position is rotated in the unlocking direction. Here, the internal gear 29 rotates counterclockwise from the state illustrated in FIG. 14. The counterclockwise rotation of the internal gear 29 brings the tooth Za3 of the internal gear 29 into contact with the tooth Zb4 of the gear portion 21*cg*, whereby the pressing member 21*cp* is rotated counterclockwise.

Further rotating the internal gear 29 counterclockwise unfixes the driving wire W from the coupling unit 21*c*. The operation of the internal gear 29 and the pressing member 21*cp* here is reverse to the operation described above. In other words, the driving wire W is unfixed from the coupling unit 21*c* by an operation reverse to the foregoing operation in fixing the driving wire W by the coupling unit 21*c*.

The foregoing operation is performed by each of the first to ninth coupling units (21*c*11 to 21*c*33). More specifically, in the process of the operation unit 400 moving from the detachment position to the fixed position, the first to ninth coupling units (21*c*11 to 21*c*33) are shifted from the unlocked state to the locked state by the movement (rotation) of the operation unit 400. In the process of the operation unit 400 moving from the fixed position to the unlocked position, the first to ninth coupling units (21*c*11 to 21*c*33) are shifted from the locked state to the unlocked state by the movement (rotation) of the operation unit 400. In other words, the user can switch the unlocked state and the locked state of the plurality of coupling units by operating a single operation unit 400.

In other words, there is no need to provide operation units for switching the unlocked state and the locked state of the respective plurality of coupling units and for the user to operate such operation units. The user can thus easily attach and detach the catheter unit 100 to/from the base unit 200. Moreover, the medical device 1 can be simplified.

The state where the first to ninth driving wires (W11 to W33) are fixed by the first to ninth coupling units (21*c*11 to 21*c*33), respectively, will be referred to as a first state. The state where the first to ninth driving wires (W11 to W33) are unfixed from the first to ninth coupling units (21*c*11 to 21*c*33), respectively, will be referred to as a second state.

The first state and the second state are switched in an interlocked manner with the movement of the operation unit 400. More specifically, the first state and the second state are switched in an interlocked manner with the movement of the operation unit 400 between the detachment position and the fixed position.

The internal gear 29 is configured to move in an interlocked manner with the operation unit 400. In the present exemplary embodiment, the joint 28 functions as a transmission member for interlocking the operation unit 400 with the internal gear 29. The internal gear 29 and the joint 28 have a function as an interlocking unit to move in an interlocked manner with the operation unit 400 so that the first state and the second state are switched in an interlocked manner with the movement of the operation unit 400.

Specifically, the internal gear 29 and the joint 28 move a part of the plate spring 21*ch* (portion to be pressed 21*chb*) with respect to the portion to be held Wa in an interlocked manner with the movement of the operation unit 400 in the state where the catheter unit 100 is attached to the base unit 200. The movement of the portion to be held 21*chb* switches the locked state and the unlocked state of the coupling unit 21*c*.

The internal gear 29 may be configured to be directly moved by the operation unit 400. In such a case, the internal gear 29 has the function as the interlocking unit.

<Movement of Operation Unit>

The movement of the operation unit 400 will be described with reference to FIGS. 15A to 15C, 16A to 16C, and 17A to 17C.

In the present exemplary embodiment, the operation unit 400 is configured to be movable between the detachment position, the unlocked position, and the fixed position in the state where the catheter unit 100 is attached to the base unit 200. The unlocked position is located between the detachment position and the fixed position.

In the present exemplary embodiment, the operation unit 400 switches the first state and the second state in an interlocked manner with the movement of the operation unit 400 between the unlocked position and the fixed position.

In the present exemplary embodiment, the operation unit 400 can move between the detachment position and the fixed position by moving in a direction different from the attachment and detachment direction DE. The operation unit 400 moves between the detachment position and the fixed position by moving in a direction intersecting (desirably, a direction orthogonal to) the attachment and detachment direction DE. In the present exemplary embodiment, the operation unit 400 moves between the detachment position and the fixed position by rotating about the rotation axis 400*r* extending in the attachment and detachment direction DE. This provides favorable operability when the user operates the operation unit 400.

Figure 15A:
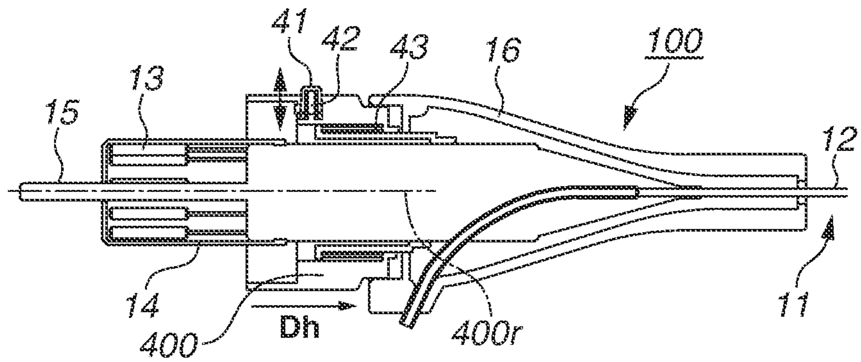
FIG. 15A is an explanatory diagram of the catheter unit and the base unit.
Figure 15B:
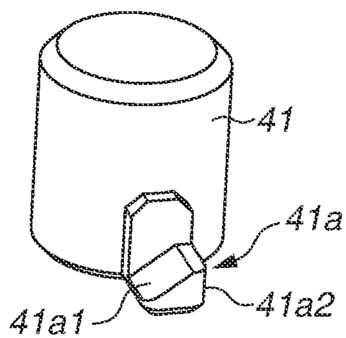
FIG. 15B is an explanatory diagram of the catheter unit and the base unit.
Figure 15C:
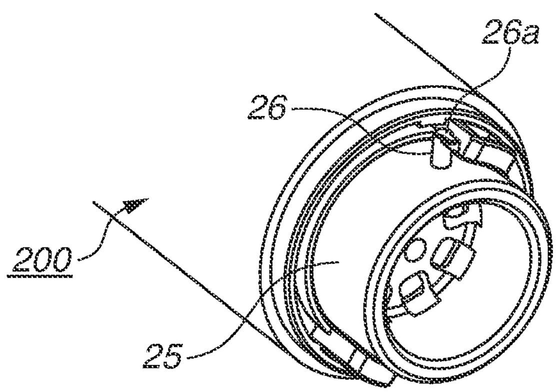
FIG. 15C is an explanatory diagram of the catheter unit and the base unit.

FIGS. 15A to 15C are explanatory diagrams of the catheter unit 100 and the base unit 200. FIG. 15A is a sectional view of the catheter unit 100. FIG. 15B is a perspective view of a button 41. FIG. 15C is a perspective view of the base unit 200.

Figure 16A:
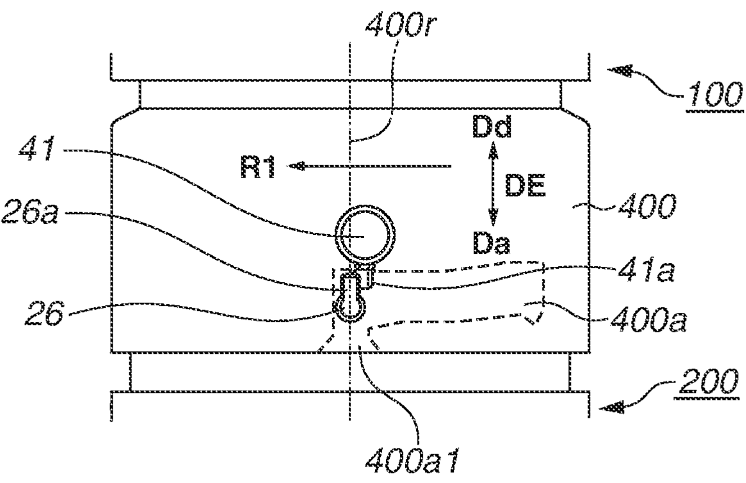
FIG. 16A is a diagram for describing an operation of an operation unit.
Figure 16B:
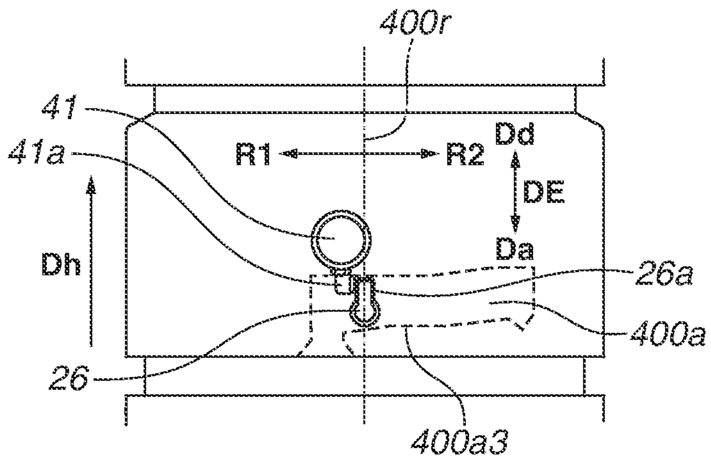
FIG. 16B is a diagram for describing the operation of the operation unit.
Figure 16C:
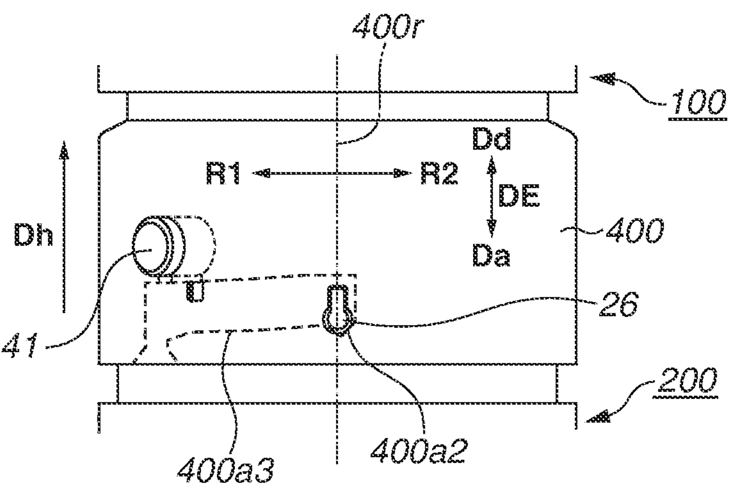
FIG. 16C is a diagram for describing the operation of the operation unit.

FIGS. 16A to 16C are diagrams for describing an operation of the operation unit 400. FIG. 16A is a diagram illustrating a state where the operation unit 400 is at the detachment position. FIG. 16B is a diagram illustrating a state where the operation unit 400 is at the unlocked position. FIG. 16C is a diagram illustrating a state where the operation unit 400 is at the fixed position.

Figure 17A:
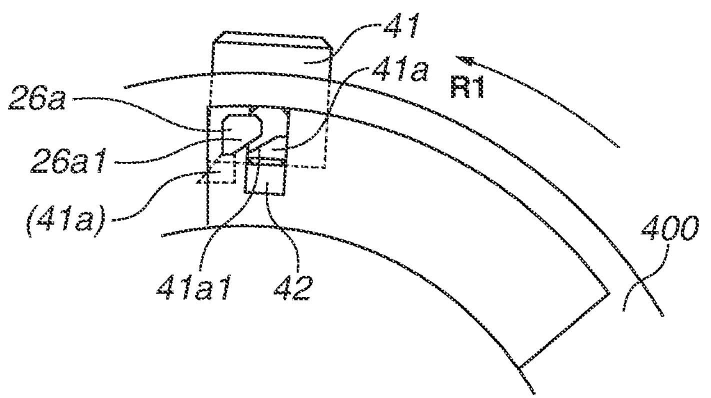
FIG. 17A is a sectional view for describing the operation of the operation unit.
Figure 17B:
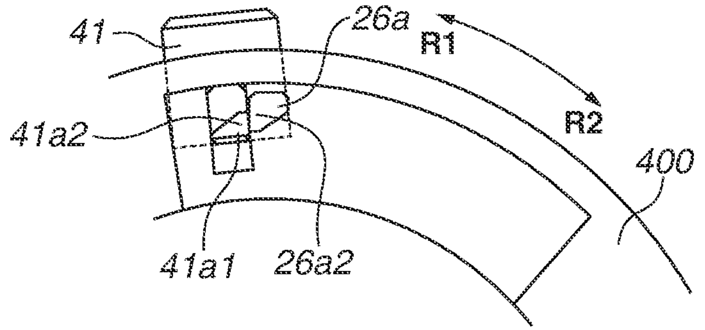
FIG. 17B is a sectional view for describing the operation of the operation unit.
Figure 17C:
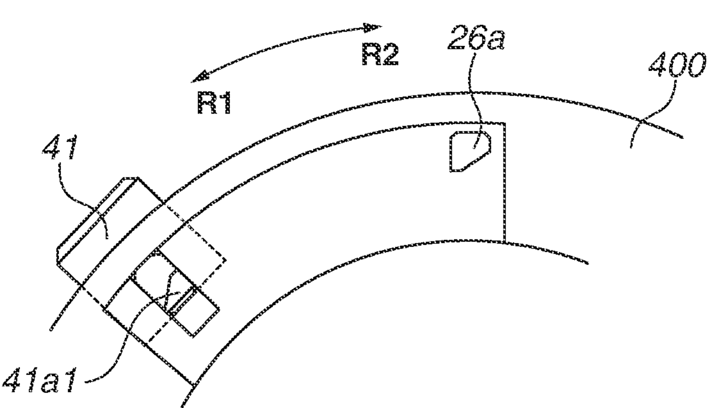
FIG. 17C is a sectional view for describing the operation of the operation unit.

FIGS. 17A to 17C are sectional views for describing the operation of the operation unit 400. FIG. 17A is a sectional view illustrating the state where the operation unit 400 is at the detachment position. FIG. 17B is a sectional view illustrating the state where the operation unit 400 is at the unlocked position. FIG. 17C is a sectional view illustrating the state where the operation unit 400 is at the fixed position.

When the operation unit 400 is at the fixed position, the coupling units 21*c* are in the locked state, and the portions to be held Wa of the driving wires W are fixed to the corresponding coupling units 21*c* (see FIG. 14).

When the operation unit 400 is at the unlocked position, the coupling units 21*c* are in the unlocked state, and the portions to be held Wa of the driving wires W and the coupling units 21*c* are unlocked (see FIG. 11). In such a state, the driving wires W and the wire driving unit 300 are disconnected. When the catheter 11 undergoes external force, the bending unit 12 can thus bend freely without resistance from the wire driving unit 300.

When the operation unit 400 is at the detachment position, the catheter unit 100 can be detached from the base unit 200. In the state where the operation unit 400 is at the detachment position, the catheter unit 100 can be attached to the base unit 200. When the operation unit 400 is at the detachment position, the coupling units 21*c* are in the unlocked state, and the portions to be held Wa of the driving wires W and the coupling units 21*c* are unlocked (see FIG. 10).

As illustrated in FIG. 15A, the catheter unit 100 includes an operation unit biasing spring 43 for biasing the operation unit 400, the button 41 serving as a moving member, and a button spring 42 for biasing the button 41.

In the present exemplary embodiment, the operation unit biasing spring 43 is a compression spring. The operation unit 400 is biased in a direction Dh toward the proximal end cover 16 by the operation unit biasing spring 43.

In the present exemplary embodiment, the button 41 and the button spring 42 are provided to the operation unit 400. When the operation unit 400 moves to the detachment position, the unlocked position, and the fixed position, the button 41 and the button spring 42 move with the operation unit 400.

The button 41 is configured to be movable with respect to the operation unit 400 in a direction intersecting the direction of the rotation axis 400*r* of the operation unit 400. The button 41 is biased outward of the catheter unit 100 (in a direction away from the rotation axis 400*r*) by the button spring 42.

As will be described below, the button 41 restricts movement of the operation unit 400 from the unlocked position to the detachment position. The movement of the operation unit 400 from the unlocked position to the detachment position is allowed by moving the button 41 with respect to the operation unit 400.

The button 41 includes a button protrusion (portion to be restricted) 41*a*. The button protrusion 41*a* includes a button slope 41*a*1 and a surface to be restricted 41*a*2.

The base unit 200 includes the base frame 25. The base frame 25 includes lock shafts 26. The lock shafts 26 have a lock protrusion (restriction portion) 26*a*.

In the present exemplary embodiment, there is a plurality (in the present exemplary embodiment, two) of lock shafts 26. All the lock shafts 26 may have a lock protrusion 26*a*. Some of the lock shafts 26 may be without a lock protrusion 26*a*.

As illustrated in FIGS. 9, 16A, 16B, and 16C, lock grooves 400*a* to be engaged with the lock shafts 26 are formed inside the operation unit 400. The lock grooves 400*a* extend in a direction different from the attachment and detachment direction DE. In the present exemplary embodiment, the lock grooves 400*a* extend in the direction of rotation of the operation unit 400. The lock grooves 400*a* can be said to extend in a direction intersecting (direction orthogonal to) the attachment and detachment direction DE.

If there is a plurality of lock shafts 26, a lock groove 400*a* is formed for each of the lock shafts 26.

As illustrated in FIG. 16A, when the catheter unit 100 is attached to the base unit 200, the lock shafts 26 are engaged with the lock grooves 400*a* via inlets 400*a*1 of the lock grooves 400*a*.

Here, the operation unit 400 is located at the detachment position and the coupling units 21*c* are in the unlocked state (see FIG. 10). In such a state, the first to ninth driving wires (W11 to W33) are therefore unfixed from the first to ninth coupling units (21*c*11 to 21*c*33), respectively. As illustrated in FIG. 17A, the button protrusion 41*a* is opposed to the lock protrusion 26*a*.

If the operation unit 400 is at the detachment position and rotated in a locking direction R1, the slope 41*a*1 of the button protrusion 41*a* comes into contact with a slope 26*a*1 of the lock protrusion 26*a*. The button 41 moves inward of the operation unit 400 (in a direction toward the rotation axis 400*r*) against the biasing force of the button spring 42. The button protrusion 41*a* then moves beyond the lock protrusion 26*a*, and the operation unit 400 moves to the unlocked position (see FIG. 17B).

Here, the coupling units 21*c* are in the unlocked state (see FIG. 11). In such a state, the first to ninth driving wires (W11 to W33) are therefore unlocked from the first to ninth coupling units (21*c*11 to 21*c*33), respectively.

In the present exemplary embodiment, the movement of the operation unit 400 from the detachment position to the unlocked position is allowed without operating the button 41. In other words, in moving the operation unit 400 from the detachment position to the unlocked position, the user does not need to operate the button 41.

If the operation unit 400 is located at the unlocked position and rotated in the locking direction R1, the operation unit 400 moves to the fixed position. In the state where the operation unit 400 is at the fixed position, positioning portions 400*a*2 of the lock grooves 400*a* are located at positions corresponding to the lock shafts 26. The operation unit 400 is biased in the direction Dh toward the proximal end cover 16 by the operation unit biasing spring 43. As a result, the positioning portions 400*a*2 are engaged with the lock shafts 26.

In the process of the operation unit 400 moving from the unlocked position to the fixed position, the portions to be held Wa of the driving wires W are fixed to the coupling units 21*c* as described above.

In the state where the operation unit is located at the fixed position, the coupling units 21*c* are in the locked state (see FIG. 14). The first to ninth driving wires (W11 to W33) are therefore fixed to the first to ninth coupling units (21*c*11 to 21*c*33), respectively. In such a state, the driving force from the wire driving unit 300 can be transmitted to the bending driving unit 13. Specifically, the driving force from the first to ninth driving sources (M11 to M33) can be transmitted to the first to ninth driving wires (W11 to W33) via the first to ninth coupling units (21*c*11 to 21*c*33), respectively.

When the operation unit 400 is at the unlocked position, walls 400*a*3 of the lock grooves 400*a* are located upstream of the lock shafts 26 in the detachment direction Dd of the catheter unit 100. When the operation unit 400 is at the fixed position, the positioning portions 400*a*2 are located upstream of the lock shafts 26 in the detachment direction Dd. As a result, the detachment of the catheter unit 100 from the base unit 200 is restricted when the operation unit 400 is at the unlocked position and when the operation unit 400 is at the fixed position. On the other hand, when the operation unit 400 is at the detachment position, the inlets 400*a*1 of the lock grooves 400*a* are located upstream of the lock shafts 26 in the detachment direction Dd. As a result, the catheter unit 100 can be detached from the base unit 200.

If the operation unit 400 is at the fixed position and rotated in an unlocking direction R2, the operation unit 400 is located at the unlocked position. In the process of the operation unit 400 moving from the fixed position to the unlocked position, the portions to be held Wa of the driving wires W are released from the coupling units 21*c* as described above.

In the state where the operation unit 400 is located at the unlocked position, the surface to be restricted 41*a*2 of the button protrusion 41*a* is in contact with the restriction surface 26*a*2 of the lock protrusion 26*a* (see FIG. 17B). In such a state, the rotation of the operation unit 400 in the unlocking direction R2 is restricted. The detachment of the catheter unit 100 from the base unit 200 is also restricted.

If the user presses the button 41 inward of the operation unit 400 with the operation unit 400 located at the unlocked position, the surface to be restricted 41*a*2 is separated from the restriction surface 26*a*2 and the button protrusion 41*a* moves beyond the lock protrusion 26*a*. As a result, the operation unit 400 can be rotated in the unlocking direction R2, and the operation unit 400 can be moved from the unlocked position to the detachment position.

When the operation unit 400 is located at the detachment position, the coupling units 21*c* are in the unlocked state. This can reduce the load acting on the driving wires W (for example, resistance from the coupling units 21*c*) in detaching and attaching the catheter unit 100 from/to the base unit 200. The user can thus easily attach and detach the catheter unit 100.

When the operation unit 400 is located at the unlocked position, the detachment of the catheter unit 100 from the base unit 200 is restricted and the coupling units 21*c* are in the unlocked state. As described above, when the coupling units 21*c* are in the unlocked state, the driving wires W and the wire driving unit 300 are disconnected, and the bending unit 12 can bend freely without resistance from the wire driving unit 300.

The user can stop the driving of the catheter 11 by the wire driving unit 300 by situating the operation unit 400 at the unlocked position in a state where the catheter 11 is inserted into the subject. Moreover, the user can hold the base unit 200 and pull the catheter 11 out of the subject since the detachment of the catheter unit 100 from the base unit 200 is restricted.

In the configuration according to the present exemplary embodiment, the movement of the operation unit 400 from the unlocked position to the detachment position is restricted unless the button 41 is operated. This can prevent the user from accidentally moving the operation unit 400 to the detachment position in moving the operation unit 400 from the fixed position to the unlocked position.

In the present exemplary embodiment, both the number of lock protrusions 26*a* and the number of buttons 41 are one. However, the medical device 1 may include a plurality of lock protrusions 26*a* and a plurality of buttons 41.

The present invention is not limited to the above embodiments and various changes and modifications can be made within the spirit and scope of the present invention. Therefore, to apprise the public of the scope of the present invention, the following claims are made.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A medical device comprising:

a main body driving unit including a plurality of driving sources;

a base unit including a coupling device connected to the main body driving unit, the coupling device including a plurality of coupling units, each of the plurality of coupling units being connected to each of the plurality of driving sources;

a bendable unit configured to be detachably attached to the base unit, the bendable unit including a bending unit and a bending driving unit configured to receive driving force of the main body driving unit via the coupling device and bend the bending unit, the bending driving unit including a plurality of linear members connected to the bending unit; and an operation unit configured to be movable between a fixed position and a detachment position in a state where the bendable unit is attached to the base unit, wherein a state where each of the plurality of linear members is fixed by each of the plurality of coupling units and a state where each of the plurality of linear members is unfixed from each of the plurality of coupling units are switched in an interlocked manner with movement of the operation unit, wherein each of the plurality of linear members is fixed to each of the plurality of coupling units so that detachment of the bendable unit from the base unit is restricted and the driving force is transmitted to the bending driving unit in a state where the bendable unit is attached to the base unit and the operation unit is located at the fixed position, wherein the detachment of the bendable unit from the base unit is allowed and each of the plurality of linear members is unfixed from each of the plurality of coupling units in a state where the bendable unit is attached to the base unit and the operation unit is located at the detachment position, wherein the plurality of linear members each includes a portion to be held, wherein the plurality of coupling units each includes a holding portion configured to hold the portion to be held, and wherein the base unit includes an interlocking unit configured to move a part of the holding portion with respect to the portion to be held in an interlocked manner with the movement of the operation unit, and wherein the interlocking unit includes a moving gear, wherein the plurality of coupling units each includes a gear portion configured to mesh with the moving gear and a pressing portion configured to press the holding portion.

2. The medical device according to claim 1, wherein the operation unit is configured to be movable between the fixed position, the detachment position, and an unlocked position, and wherein the detachment of the bendable unit from the base unit is restricted and each of the plurality of linear members is unfixed from each of the plurality of coupling units in a state where the bendable unit is attached to the base unit and the operation unit is located at the unlocked position.

3. The medical device according to claim 2, wherein a moving member is configured to be movable with respect to the operation unit and restrict movement of the operation unit from the unlocked position to the detachment position, and wherein the movement of the operation unit from the unlocked position to the detachment position is allowed by moving the moving member with respect to the operation unit.

4. The medical device according to claim 3, wherein the operation unit is provided to the bendable unit, wherein the base unit includes a restriction unit, and wherein the moving member is configured to be movable with the operation unit and includes a portion to be restricted, the portion to be restricted being restricted by the restriction unit so that the movement of the operation unit from the unlocked position to the detachment position is restricted.

5. The medical device according to claim 1, wherein the pressing portion is configured to be movable between a pressing position where the pressing portion presses the holding portion and a retracted position where the pressing portion is retracted from the pressing position by the gear portion being moved by the moving gear, wherein the portion to be held is fixed by the holding portion in a case where the pressing portion is at the pressing position, and wherein the portion to be held is unfixed from the holding portion in a case where the pressing portion is at the retracted position.

6. The medical device according to claim 1, wherein the operation unit is configured to be rotatable about a rotation axis extending in an attachment and detachment direction of the bendable unit.

7. The medical device according to claim 1, wherein the base unit includes a key receptor portion, wherein the bendable unit includes a key configured to be engageable with the key receptor portion, and wherein movement of the bendable unit with respect to the base unit in a circumferential direction of a circle on which the plurality of linear members is arranged is restricted by engagement of the key with the key receptor portion.

8. The medical device according to claim 1, wherein the bendable unit includes a cover configured to cover the plurality of linear members, and wherein the cover is configured to be movable between a cover position where the cover covers the plurality of linear members and a cover-retracted position where the cover is retracted from the cover position.

9. The medical device according to claim 1, wherein the operation unit is configured to be rotatable about a rotation axis extending in an attachment and detachment direction of the bendable unit.

10. The medical device according to claim 2, wherein the operation unit is configured to be rotatable about a rotation axis extending in an attachment and detachment direction of the bendable unit.

11. The medical device according to claim 3, wherein the operation unit is configured to be rotatable about a rotation axis extending in an attachment and detachment direction of the bendable unit.

12. The medical device according to claim 4, wherein the operation unit is configured to be rotatable about a rotation axis extending in an attachment and detachment direction of the bendable unit.

13. The medical device according to claim 5, wherein the operation unit is configured to be rotatable about a rotation axis extending in an attachment and detachment direction of the bendable unit.

14. A bendable unit configured to be detachably attached to a base unit, the base unit including a main body driving unit including a plurality of driving sources, and a coupling device connected to the main body driving unit, the coupling device including a plurality of coupling units, each of the plurality of coupling units being connected to each of the plurality of driving sources, the bendable unit comprising:

a bending unit;

a bending driving unit configured to receive driving force of the main body driving unit via the coupling device and bend the bending unit, the bending driving unit including a plurality of linear members connected to the bending unit; and an operation unit configured to be movable between a fixed position and a detachment position in a state where the bendable unit is attached to the base unit, wherein a state where each of the plurality of linear members is fixed by each of the plurality of coupling units and a state where each of the plurality of linear members is unfixed from each of the plurality of coupling units are switched in an interlocked manner with movement of the operation unit, wherein each of the plurality of linear members is fixed to each of the plurality of coupling units so that detachment of the bendable unit from the base unit is restricted and the driving force is transmitted to the bending driving unit in a state where the bendable unit is attached to the base unit and the operation unit is located at the fixed position, wherein the detachment of the bendable unit from the base unit is allowed and each of the plurality of linear members is unfixed from each of the plurality of coupling units in a state where the bendable unit is attached to the base unit and the operation unit is located at the detachment position, wherein the plurality of linear members each includes a portion to be held, wherein the plurality of coupling units each includes a holding portion configured to hold the portion to be held, and wherein the base unit includes an interlocking unit configured to move a part of the holding portion with respect to the portion to be held in an interlocked manner with the movement of the operation unit, and wherein the interlocking unit includes a moving gear, wherein the plurality of coupling units each includes a gear portion configured to mesh with the moving gear and a pressing portion configured to press the holding portion.

* * * * *